(12) United States Patent
Koga et al.

(10) Patent No.: US 6,221,868 B1
(45) Date of Patent: Apr. 24, 2001

(54) REMEDIES/PREVENTIVES FOR FREQUENT URINATION/URINARY INCONTINENCE AND TROPONE DERIVATIVES

(75) Inventors: Ichiro Koga; Kazuhisa Narita; Atsushi Okada, all of Saitama (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/446,423

(22) PCT Filed: Jun. 26, 1998

(86) PCT No.: PCT/JP98/02865

§ 371 Date: Dec. 20, 1999

§ 102(e) Date: Dec. 20, 1999

(87) PCT Pub. No.: WO99/00366

PCT Pub. Date: Jan. 7, 1999

(30) Foreign Application Priority Data

Jun. 27, 1997 (JP) .................................................. 9-186030
Aug. 8, 1997 (JP) .................................................. 9-225552
Sep. 5, 1997 (JP) .................................................. 9-256223

(51) Int. Cl.[7] ..................... C07D 211/14; C07D 213/74; A61K 31/445; A61K 31/495; A61P 15/00
(52) U.S. Cl. ................... 514/252.13; 544/392; 544/403; 514/255.03
(58) Field of Search .................................. 544/392, 403; 514/255.03, 252.13

(56) References Cited

U.S. PATENT DOCUMENTS 4,203,986 * 5/1980 Joullie et al. .................... 424/250

FOREIGN PATENT DOCUMENTS 60-228414  11/1985 (JP) .
92/4338   3/1991 (WO) .

OTHER PUBLICATIONS

David A.B., "Blockade of colchicine-incuded inhibition of vasopressin-simulated osmotic water flow: failure to influence microtubule formation". A.J. Physiol., 249, F464–9 (1985).

* cited by examiner

Primary Examiner—Mukund J. Shah
Assistant Examiner—Hong Liu
(74) Attorney, Agent, or Firm—Nields & Lemack

(57) ABSTRACT

Remedies/preventives (therapeutic or preventive agents) against frequent urination (pollakiuria)/urinary incontinence which contain as an active ingredient compound having a tropone structure or pharmacologically acceptable salt thereof and a novel compound having the tropone structure. The compounds having a tropone structure and having the above pharmacological effects are those represented by, for example, general (1):

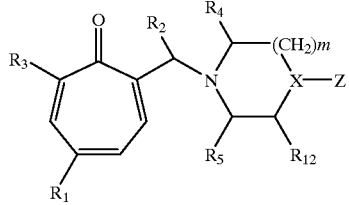

(1)

wherein $R_1$ and $R_2$ represent each a hydrogen atom, lower alkyl group, etc., $R_3$ represents —OR or —$NR_2$; $R_4$, $R_5$ and $R_{12}$ represents each a hydrogen atom or a lower alkyl group, X represents a nitrogen atom or CH, Z represents —$CHAr_2$, an unsubstituted or substituted phenyl, etc. m is 1 or 2. These compounds are novel ones excluding those wherein Z is —$CHAr_2$.

16 Claims, No Drawings

REMEDIES/PREVENTIVES FOR FREQUENT URINATION/URINARY INCONTINENCE AND TROPONE DERIVATIVES

DESCRIPTION

1. Technical Field

The present invention relates to a pharmaceutical preparation comprising a compound having a tropone structure and in particular to remedies/preventives (therapeutic or preventive agents) against frequent urination (pollakiuria) or urinary incontinence.

2. Background Art

With the aging society, pollakiuria, urinary incontinence, and dementia become a social problem. There is a need for medical care with the aim of maintaining QOL (quality of life) in one's old age. In particular, pollakiuria and urinary incontinence limit the range of behavior for the aged and significantly lower their quality of life, thus bringing about a very heavy burden not only on a patient but also on a nurse or a care worker.

Tropone compounds including hinokitiol are marketed as a part of daily articles as a bathing agent and a humectant. Further, they are extensively studied as pharmaceutical preparations. For example, JP-A 6-509318 discloses such compounds as therapeutic and preventive agents against ischemic diseases such as cerebral vascular diseases and heart vascular diseases. However, the effect of the compounds having a tropone structure on pollakiuria and urinary incontinence is not known.

As chemicals for treatment of diseases such as pollakiuria and urinary incontinance, an anticholinergic agent, a smooth muscle direct relaxant, a, tricyclic antidepressant, etc. have been used, but the action of the smooth muscle direct relaxant on the bladder is lower as that of the anticholinergic agent, and the effect thereof on urinary incontinence is unsatisfactory. Further, the anticholinergic agent has the side effects of dry mouth, ischuria, etc. In the change of the human bladder smooth muscle along with aging, an increase in atropine resistance contraction is observed, and these chemicals are not necessarily adequate in respect of the effect and side effects. In particular, the chemicals alone having an anticholinergic action are considered unsatisfactory in their effect on urinary incontinence for the aged. In the clinical field of chemotherapy at present under these circumstances, development of a new therapeutic agent for pollakiuria and urinary incontinence is desired earnestly. Further, with the highly aging society near at hand, comprehensive therapy came to be conducted for nerve diseases such as cerebral apoplexy, spinal damage or nerve-degenerated disease, and further collective therapy for uterine cancer and rectal cancer and therapy for diabetes have been developed thereby enabling the prolonging of the life of a fatal patient in the past, and as a result and also for raising the QOL of the patient, there is an increasing need for treatment and prevention of pollakiuria and urinary incontinence.

DISCLOSURE OF THE INVENTION

As a result of eager study to solve the problem described above, the present inventors unexpectedly found that compounds having a tropone structure have the following effects: (1) they increase the bladder capacity by their inhibitory action on urination reflexes, thus prolonging urination intervals, (2) they do not cause dry mouth and ischuria as the side effects of the anticholinergic agent, and (3) they are also effective for patients observed to have an increase in atropine resistance contraction and the like, and the present inventors found that these compounds are effective as a therapeutic and preventive agent against pollakiuria and urinary incontinence, and the present invention was thereby completed. That is, the present invention relates to the following items 1 to 19.

1. A therapeutic or preventive agent against pollakiuria or urinary incontinence, comprising a compound having a tropone structure or a pharmaceutically acceptable salt thereof as an active ingredient.

2. The therapeutic or preventive agent against pollakiuria or urinary incontinence according to item 1 above, wherein the tropone compound or a pharmaceutically acceptable salt thereof used as an active ingredient has 1 to 3 substituent groups on the tropone structure, and at least one of the substituent groups is a lower alkyl group substituted with a 6- to 7-membered cyclic group having at least one nitrogen atom in the ring, and when there are 2 or more substituent groups, each of the substituent groups is independently a $C_1$ to $C_{20}$ hydrocarbon residue bound via or not via a hetero atom to the tropone structure.

3. The therapeutic or preventive agent against pollakiuria or urinary incontinence according to item 1 or 2 above, wherein the compound having a tropone structure is a compound represented by the general formula (1):

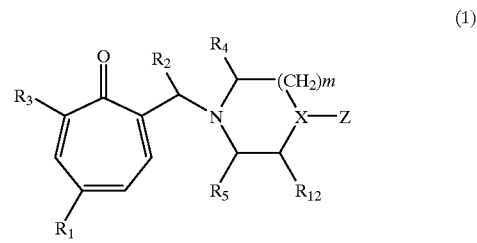

(1)

wherein $R_1$ and $R_2$ are the same or different and represent a hydrogen atom, a substituted or unsubstituted lower alkyl group, a substituted or unsubstituted aryl group, $R_3$ represents —OR or —$NR_7$—$R_8$, $R_6$ represents a hydrogen atom, a substituted or unsubstituted lower alkyl group, a substituted or unsubstituted aralkyl group or a substituted or unsubstituted $C_1$ to $C_5$ acyl group, $R_7$ and $R_8$ are the same or different and represent a hydrogen atom, a lower alkyl group which may be substituted with a hetero atom, or a substituted or unsubstituted aralkyl group, or $R_7$ and $R_8$ are combined to form a 5- to 10-membered ring which may contain 1 to 3 —O— or —$NR_9$— residues, $R_9$ represents a hydrogen atom, a substituted or unsubstituted lower alkyl group or a substituted or unsubstituted aryl group; $R_4$ and $R_5$ are the same or different and represent a hydrogen atom or a lower alkyl group, $R_{12}$ represents a hydrogen atom and a lower alkyl group, X represents a nitrogen atom or CH, Z represents —$CH(Ar_1)(Ar_2)$, an unsubstituted or substituted phenyl, benzyl, benzoyl, 2-pyridyl or 2-pyrimidyl group, $Ar_1$ and $Ar_2$ are substituted or unsubstituted aryl groups which may be the same or different, and m is 1 or 2.

4. The therapeutic or preventive agent against pollakiuria or urinary incontinence according to any one of items 1 to 3 above, wherein the compound having a tropone structure is a compound represented by the general formula (2):

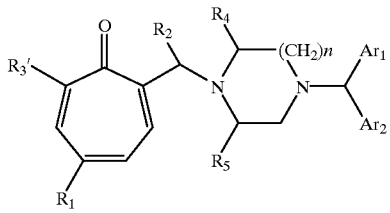

wherein $R_1$ and $R_2$ are the same or different and represent a hydrogen atom, a lower alkyl group, a substituted or unsubstituted aryl group, $R_3'$ represents —$OR_6'$ or —$NR_7R_8$, $R_6'$ represents a hydrogen atom, a lower alkyl group which may be substituted with a hetero atom, or a substituted or unsubstituted aralkyl group, $R_7$ and $R_8$ are the same or different and represent a hydrogen atom, a lower alkyl group which may be substituted with a hetero atom, or a substituted or unsubstituted aralkyl group, or $R_7$ and $R_8$ are combined to form a 5- to 10-membered ring which may contain 1 to 3 —O— or —$NR_9$— residues, $R_9$ represents a hydrogen atom, a lower alkyl group or a substituted or unsubstituted aryl group; $R_4$ and $R_5$ are the same or different and represent a hydrogen atom or a lower alkyl group, $Ar_1$ and $Ar_2$ are the same or different and represent a substituted or unsubstituted aryl group, and n is 1 or 2.

5 The therapeutic or preventive agent against pollakiuria or urinary incontinence according to item 4 above, wherein $R_1$ represents an isopropyl group, $R_2$, $R_4$ and $R_5$ represent a hydrogen atom, $R_3'$ represents a 2-hydroxyethylamino group, $Ar_1$ and $Ar_2$ independently represent a phenyl group or a 4-fluorophenyl group, and n is 1.

6. A novel tropone derivative represented by the general formula (3):

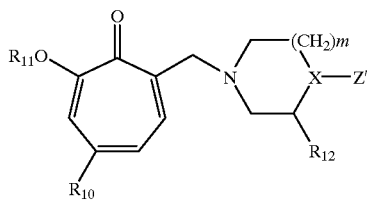

wherein $R_{10}$ represents a hydrogen atom or a $C_1$ to $C_5$ alkyl group, $R_{11}$ represents a hydrogen atom atom, a $C_1$ to $C_5$ alkyl group, a $C_1$ to $C_5$ alkyl group having a hydroxyl group or an alkoxy group, an unsubstituted or substituted benzyl group, or a $C_1$ to $C_5$ acyl group, $R_{12}$ represents a hydrogen atom or a $C_1$ to $C_3$ alkyl group, Z' represents an unsubstituted or substituted phenyl, benzyl, benzoyl, 2-pyridyl or 2-pyrimidyl group, X represents a nitrogen atom or CH, and m is an integer of 1 or 2, as well as pharmaceutically acceptable salts thereof.

7. The novel tropone derivative according to item 6 above, wherein the substituent group on benzyl, phenyl, benzoyl, 2-pyridyl or 2-pyrimidyl group in Z' is a substituent group selected from a $C_1$ to $C_5$ alkyl group, a $C_1$ to $C_5$ halogenoalkyl group, halogen, nitro group, cyano group and a lower alkoxy group, as well as pharmaceutically acceptable salts thereof.

8. The novel tropone derivative according to item 6 or 7 above, wherein $R_{10}$ represents a hydrogen atom or a $C_1$ to $C_5$ alkyl group, $R_{11}$ represents a hydrogen atom, a $C_1$ to $C_5$ alkyl group, a $C_1$ to $C_5$ alkyl group having a hydroxyl group or an alkoxy group, an unsubstituted or substituted benzyl group, or a $C_1$ to $C_5$ acyl group, $R_{12}$ represents a hydrogen atom or a $C_1$ to $C_5$ alkyl group, Z' represents an unsubstituted or substituted phenyl, 2-pyridyl or 2-pyrimidyl group, X represents a nitrogen atom, and m is an integer of 1 or 2, as well as pharmaceutically acceptable salts thereof.

9. The novel tropone derivative according to item 8 above, wherein $R_{10}$ represents an isopropyl group, $R_{11}$ represents a hydrogen atom, a $C_1$ to $C_5$ alkyl group or a benzyl group, $R_{12}$ represents a hydrogen atom, Z' represents an unsubstituted phenyl group, or a phenyl group substituted with 1 to 2 groups selected from lower alkyl groups or halogens, X represents a nitrogen atom, and m is the integer of 1, as well as pharmaceutically acceptable salts thereof.

10. The novel tropone derivative according to item 9 above, wherein $R_{11}$ is an ethyl group or a benzyl group, Z' is an unsubstituted phenyl group or a 4-fluorophenyl group, as well as pharmaceutically acceptable salts thereof.

11. A pharmaceutical composition comprising the novel tropone derivative according to any one of items 6 to 10 above or a pharmaceutically acceptable salt thereof as an active ingredient.

12. A therapeutic or preventive agent against pollakiuria or urinary incontinence, comprising the novel tropone derivative according to any one of items 6 to 10 above or a pharmaceutically acceptable salt thereof as an active ingredient.

13. A novel tropone derivative represented by the general formula (4):

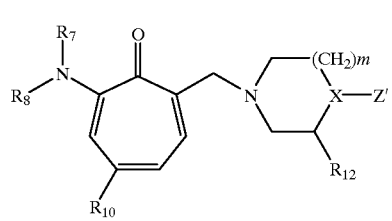

wherein $R_{10}$ represents a hydrogen atom or a $C_1$ to $C_5$ alkyl group, $R_7$ and $R_8$ are the same or different and represent a hydrogen atom, an optionally substituted lower alkyl group, or a substituted or unsubstituted aralkyl group, or $R_7$ and $R_8$ are combined to form a 5- to 10-membered ring which may contain 1 to 3 —O— or —$NR_9$— residues, $R_{12}$ represents a hydrogen atom or a $C_1$ to $C_5$ alkyl group, $R_9$ represents a hydrogen atom, lower alkyl or a substituted or unsubstituted aryl group, Z' represents an unsubstituted or substituted phenyl, benzyl, benzoyl, 2-pyridyl or 2-pyrimidyl group, X represents a nitrogen atom or CH, and m is an integer of 1 or 2, as well as pharmaceutically acceptable salts thereof.

14. The novel tropone derivative according to item 13, wherein a substituent group on a lower alkyl group in $R_7$ and $R_8$ is a substituent group selected from a hydroxyl group, a $C_1$ to $C_5$ alkoxy group and a mono- or di-alkyl amino group whereupon the number of carbon atoms in the alkyl group is 1 to 5; and a substituent group on an aralkyl group in $R_7$ and $R_8$, on an aryl group in $R_9$ or on a phenyl, benzyl, benzoyl, 2-pyridyl or 2-pyrimidyl group in Z' is a substituent group selected from a $C_1$ to $C_5$ alkyl group, halogen, a $C_1$ to $C_5$ halogenoalkyl group, nitro group, cyano group and a $C_1$ to $C_5$ lower alkoxy group, as well as pharmaceutically acceptable salts thereof.

15. The novel tropone derivative according to item 13 or 14 above, wherein $R_{10}$ represents a $C_1$ to $C_5$ alkyl group, $NR_7R_8$ represents a $C_2$ to $C_5$ alkylamino group having a hydroxyl group, Z' represents an unsubstituted or substituted phenyl group or a 2-pyridyl or 2-pyrimidyl group, X represents a nitrogen atom, and m is an integer of 1 or 2, as well as pharmaceutically acceptable salts thereof.

16. The novel tropone derivative according to item 15 above, wherein $R_{10}$ represents an isopropyl group, $NR_7R_8$ represents a 2-hydroxyethylamino group, Z' represents a phenyl group unsubstituted or substituted with 1 to 2 substituent groups selected from halogen or lower alkyl group, X represents a nitrogen atom, and m is the integer of 1, as well as pharmaceutically acceptable salts thereof.

17. The novel tropone derivative according to item 16 above, wherein Z' is unsubstituted phenyl or a 4-chlorophenyl-2-methyl group or a 4-fluorophenyl group, as well as pharmaceutically acceptable salts thereof.

18. A pharmaceutical composition comprising the novel tropone derivative according to any one of items 13 to 17 above or a pharmaceutically acceptable salt thereof as an active ingredient.

19. A therapeutic or preventive agent against pollakiuria or urinary incontinence, comprising the novel tropone derivative according to any one of items 13 to 17 or a pharmaceutically acceptable salt thereof as an active ingredient.

BEST MODE FOR CARRYING OUT THE INVENTION

The compounds having a tropone structure in the present invention are not particularly limited insofar as they have an inhibitory action on urination reflexes, and such compounds are preferably tropone compounds usually having 1 to 3 substituent groups on the tropone structure thereof wherein at least one of said substituent groups is a lower alkyl group substituted with a 6- or 7-membered cyclic group having at least one nitrogen atom in the ring, and when there are 2 or more substituent groups, each of the substituent groups is independently a $C_1$ to $C_{10}$ hydrocarbon residue bound via or not via a hetero atom to the tropone structure, or pharmaceutically acceptable salts thereof. The positions of such substituent groups on the tropone structure are the 2-position, 4-position and 7-position, and if there are 3 substituent groups, the compounds are preferably those wherein a $C_1$ to $C_{20}$ hydrocarbon residue is bound at the 2-position via a hetero atom to the tropone structure, a $C_1$ to $C_{20}$ hydrocarbon residue is bound at the 4-position not via a hetero atom to the tropone structure, and a lower alkyl group substituted with a 6- or 7-membered cyclic group having at least one nitrogen atom in the ring is bound at the 7-position. These preferable compounds are for examples those of the general formula (1).

The 6- or 7-membered cyclic group having at least one nitrogen atom in the ring may contain hetero atoms other than said nitrogen atom, and the number of hetero atoms including the nitrogen atom is preferably 1 to 3. Specifically, piperidino, piperazino and morpholino groups are mentioned. When these groups are present on an alkyl group, the alkyl group is substituted preferably with these groups at nitrogen atom contained in the ring.

The lower alkyl group substituted with a 6- or 7-membered cyclic group having at least one nitrogen atom in the ring is preferably a group substituted at the 7-position on the tropone structure of the general formula (1). Specific examples thereof are as follows:
4-(diphenylmethyl)piperazino-1-methyl
4-bis(4-fluorophenyl)methylpiperazino-1-methyl
4-bis(4-chlorophenyl)methylpiperazino-1-methyl
4-bis(4-methoxyphenyl)methylpiperazino-1-methyl
4-bis(2-nitrophenyl)methylpiperazino-1-methyl
4-bis(2-methylpinly)methylpiperazino-1-methyl
4-benzylpiperidino-1-methyl
4-benzoylpiperidino-1-methyl
4-benzylpiperazino-1-methyl
4-phenylpiperazino-1-methyl
4-(2-chlorophenyl)piperazino-1-methyl
4-(3-chiorophenyl)piperazinol-methyl
4-(3-fluorophenyl)piperazino-1-methyl
4-(4-fluorophenyl)piperazino-1-methyl
4-(4-methylphenyl)piperazino-1-methyl
4-(3-methylphenyl)piperazino-1-methyl
4-(2-methoxyphenyl)piperazino-1-methyl
4-(4-methoxyphenyl)piperazino-1-methyl
4-(4-nitrophenyl)piperazino-1-methyl
4-(2-methyithiophenyl)piperazino-1-methyl
4-(2,4-dimethylphenyl)piperazino-1-methyl
4-phenyl-3-methylpiperazino-1-methyl
4-(4-chloro-2-methyl)phenylpiperazino-1-methyl The $C_1$ to $C_{20}$ hydrocarbon residue may be branched, not branched, saturated or unsaturated and linear or cyclic, and the cyclic residue may contain about 1 to 3 hetero atoms. These include substituted or unsubstituted alkyl groups, substituted or unsubstituted aryl groups, and 3- to 10-membered, saturated or unsubstituted cyclic groups (including heterocyclic groups). These groups which are bound via a hetero atom to the tropone ring include e.g. $R_3$ in the general formula (1), that is, $—OR_6$ or $—NR_7R_8$ ($R_6$, $R_7$ and $R_8$ have the same meanings as defined above).

The lower alkyl group includes e.g. $C_1$ to $C_5$ alkyl groups such as methyl, ethyl, n-propyl, isopropyl, n-butyl, isobutyl, n-pentyl and isoamyl. In the present invention, an alkyl group in a lower alkyl group etc. may possess substituent groups. The substituent groups on the alkyl group include, but are not limited to, usually, halogen, nitro group, cyano group, amino group, a mono- or di-lower alkyl-substituted amino group, hydroxy group, a lower alkoxy group, an acyl group, an aryl group, a 3- to 10-membered heterocyclic group.

The aryl group includes e.g. $C_6$ to $C_{10}$ aryl groups such as phenyl group and naphthyl group. The aryl group may possess substituent groups, and the substituent groups on the aryl group include a lower alkyl group, halogen, nitro group, cyano group, amino group, a mono- or di-lower alkyl-substituted amino group, hydroxy group, a lower alkoxy group or an acyl group, and the number of substituent groups may be about 1 to 7. Examples of these aryl groups are e.g. phenyl, p-chlorophenyl, m-chlorophenyl, o-chlorophenyl, o,m-dichlorophenyl, p-fluorophenyl, m-fluorophenyl, o-fluorophenyl, p-bromophenyl, m-bromophenyl, o-bromophenyl, m-iodophenyl, p-iodophenyl, o-iodophenyl, p-trifluoromethylphenyl, p-nitrophenyl, m-nitrophenyl, p-cyanophenyl, o-cyanophenyl, p-methoxyphenyl and o,p-dimethoxyphenyl.

The halogen includes chloro, fluoro, bromo and iodo.

The lower alkoxy group includes $C_1$ to $C_5$ alkoxy groups, and specific examples include methoxy, ethoxy, n-propoxy, isopropoxy, butoxy, tert-butoxy, pentoxy, etc.

The acyl group includes usually $C_1$ to $C_{10}$, preferably $C_1$ to $C_5$ acyl groups which may possess substituent groups. As the substituent groups, those described as the substituent groups on the alkyl group can be used as such. Specific examples of the acyl group include acetyl, ethylcarbonyl, propylcarbonyl, benzoyl, etc.

The hetero atom includes oxygen, nitrogen or sulfur atoms.

The aralkyl group includes $C_7$ to $C_{20}$ aralkyl groups such as benzyl, phenethyl, etc. and these may be substituted with the same substituent groups as on the aryl group described above.

Examples of lower alkyl groups in $R_1$, $R_2$, $R_4$, $R_5$ and $R_9$ include the $C_1$ to $C_5$ alkyl groups described above.

Examples of lower alkyl groups in $R_6$, $R_6'$, $R_7$ and $R_8$, which may be substituted with hetero atoms, include e.g. unsubstituted lower alkyl groups such as methyl, ethyl, n-propyl and n-butyl, or substituted lower alkyl groups such as 2-hydroxyethyl, 3-hydroxypropyl, 2-[N,N-dimethylamino] ethyl, 3-[N,N-dimethylamino] propyl etc. having a hydroxy group, a lower alkoxy group, a mono- or di-lower alkyl amino group or the like as the substituent group.

Specific examples of —$OR_6$ or —$NR_7R_8$ include substituted or unsubstituted lower alkoxy groups such as methoxy, ethoxy, propoxy, 2-hydroxyethoxy, dimethylaminoethoxy, ect. or substituted (e.g. hydroxy-, lower alkylamino- or the like as substituents) or unsubstituted lower alkyl amino groups, such as ethylamino, propylamino, hydroxyethylamino and dimethylaminoethylamino.

Further, substituted or unsubstituted aralkyl groups in $R_6$, $R_6'$, $R_7$ and $R_8$ include those exemplified as the aralkyl group described above. Further, the heterocyclic group which $R_7$ and $R_8$ are combined to form includes a 5- to 10-membered heterocyclic group containing 1 to 3 hetero atoms in the ring. Specifically, it includes group such as pyrrolidino, piperazino, piperidino, morpholino, etc. These may be substituted with the same substituent groups as on the aryl group described above, and examples are hydroxypiperidino etc.

The aryl group in $R_9$ includes those exemplified for the aryl described above. The heterocyclic group having $R_9$ includes e.g. 4-substituted or unsubstituted lower alkylpiperazino group, such as 4-methylpiperazino and 4-benzylpiperazino, or 4-halogeno- or lower alkyl-substituted or unsubstituted arylpiperazino groups such as 4-phenylpiperazino, 4-p-chlorophenylpiperazino and 4-methylphenylpiperazino.

The aryl groups represented by $Ar_1$ and $Ar_2$ are those exemplified for the aryl group described above, such as phenyl, p-chlorophenyl, m-chlorophenyl, o-chlorophenyl, o,m-dichlorophenyl, p-fluorophenyl, m-fluorophenyl, o-fluorophenyl, p-bromophenyl, m-bromophenyl, o-bromophenyl, m-iodophenyl, p-iodophenyl, o-iodophenyl, p-trifluoromethylphenyl, p-nitrophenyl, m-nitrophenyl, p-cyanophenyl, o-cyanophenyl, p-methoxyphenyl and o,p-dimethoxyphenyl.

Among the compounds represented by the general formula (1), preferable compounds include those shown in the general formulae (2), (3) or (4).

The pharmaceutically acceptable salt of the compound having a tropone structure includes salts with mineral acids such as hydrochloric acid and sulfuric acid, organic sulfonic acids such as methanesulfonic acid and p-toluenesulfonic acid, as well as salts with organic carboxylic acid such as acetic acid, propionic acid, succinic acid, lactic acid, tartaric acid and malic acid.

The therapeutic or preventive agent against pollakiuria or urinary incontinence according to the present invention can be used alone or as a composition along with other medicines or pharmaceutical additives insofar as said compound or its pharmaceutically acceptable salt is used as the active ingredient. For example, the present compound or salt can be combined as necessary with pharmaceutically acceptable carries, excipients and diluents to prepare powder, granules, tablets, capsules and injections. The amount of the compound having a tropone structure or its pharmaceutically acceptable salt in the pharmaceutical preparation is preferably in the range of 0.01 to 100% by weight and preferably 0.1 to 90% by weight, the remainder being pharmaceutical additives. The pharmaceutical preparation can be administered via a suitable route including oral, rectal, nasal, topical (including buccal and sublingual), vaginal, bladder, parenteral (including subcutaneous, intramuscular, intravenous and cutaneous) and percutaneous (ointment, cream, paste etc.) routes. A preferable route is determined depending on the condition and age of a patient and the actual condition to be treated. The dosage is varied depending on the administration route, the condition and age of a patient and the actual condition to be treated, and for example in the case of oral administration into an adult person, 0.1 mg to 2000 mg, preferably 1 mg to 100 mg of the active ingredient can be administered daily once or in portions.

This applies when the compounds of the general formula (3) or (4) is used in a pharmaceutical composition.

The foregoing applies to the whole description of the specification. Now, the compounds represented by the general formulae (2), (3) and (4) are described.

First, the compounds represented by the general formula (2) are described.

Preferable among the compounds represented by the general formula (2) are those wherein $R_1$ represents a hydrogen atom or a $C_1$ to $C_3$ lower alkyl group such as methyl, ethyl, isopropyl, etc., preferably isopropyl, $R_2$ represents a hydrogen atom, $R_3$ represents a $C_1$ to $C_{10}$ lower alkoxy group such as methoxy, ethoxy, etc., a benzyloxy group, or a hydroxy group-containing $C_1$ to $C_5$ alkylamino group such as 2-hydroxyethylamino and 3-hydroxypropylamino, $R_4$ represents a hydrogen atom or a $C_1$ to $C_3$ lower alkyl group such as methyl, ethyl, etc., $R_5$ represents a hydrogen atom or a $C_1$ to $C_3$ lower alkyl group such as methyl, ethyl, etc., and $Ar_1$ and $Ar_2$ independently represent a phenyl group which may contain a $C_1$ to $C_3$ lower alkoxy group such as methoxy, ethoxy, etc., halogen such as chloro, fluoro, bromo, iodo, etc., a halogeno lower alkyl group such as trifluoromethyl, a cyano group or a nitro group at the o- and/or p-positions thereof.

Examples of the compounds having a tropone structure represented by the general formula (2) include:

(1) 7-[4-(diphenylmethyl)piperazino-1-methyl]-2-[(2-hydroxyethyl)amino]-4-isopropyl-2,4,6-cycloheptatrien-1-one (2) 7-[4-bis(4-fluorophenyl)methylpiperazino-1-methyl]-2-[(2-hydroxyethyl)amino]-4-isopropyl-2,4,6-cycloheptatrien-1-one (3) 7-[4-(diphenylmethyl)piperazino-1-methyl]-2-methoxy-4-isopropyl-2,4,6-cycloheptatrien-1-one (4) 7-[4-(diphenylmethyl)piperazino-1-methyl]-2-ethoxy-4-isopropyl-2,4,6-cycloheptatrien-1-one (5) 7-[4-(diphenylmethyl)piperazino-1-methyl]-2-[(2-hydroxyethyl)amino]-2,4,6-cycloheptatrien-1-one (6) 7-[4-(diphenylmethyl)piperazino-1-methyl]-4-isopropyl-2-piperidino-2,4,6-cycloheptatrien-1-one (7) 7-[4-(diphenylmethyl)piperazino-1-methyl]-4-isopropyl-2-morpholino-2,4,6-cycloheptatrien-1-one (8) 7-[4-(diphenylmethyl)piperazino-1-methyl]-2-(4-hydroxypiperidino)-4-isopropyl-2,4,6-cycloheptatrien-1-one (9) 2-[2-(dimethylamino)ethylamino]-7-[4-(diphenylmethyl)piperazino-1-methyl]-4-isopropyl-2,4,6-cycloheptatrien-1-one

(10) 2-benzyloxy-7-[4-(diphenylmethyl)piperazino-1-methyl]-4-isopropyl-2,4,6-cycloheptatrien-1-one

(11) 2-[2-(dimnethylamino)ethoxy]-7-[4-(diphenylmethyl) piperazino-1-methyl]-4-isopropyl-2,4,6-cycloheptatrien-1-one
(12) 7-[4-bis(4-chlorophenyl)methylpiperazino-1-methyl]-2-[(2-hydroxyethyl)amino1-4-isopropyl-2,4,6-cycloheptatrien-1-one
(13) 7-[4-bis(3-chlorophenyl)methylpiperazino-1-methyl]-2-[(2-hydroxyethyl)amino]-4-isopropyl-2,4,6-cycloheptatrien-1-one
(14) 7-[4-bis(4-methoxyphenyl)methylpiperazino-1-methyl]-2-[(2-hydroxyethyl)amino]-4-isopropyl-2,4,6-cycloheptatrien-1-one
(15) 7-[4-bis(2-methoxyphenyl)methylpiperazino-1-methyl]-2-[(2-hydroxyethyl)amino]-4-isopropyl-2,4,6-cycloheptatrien-1-one
(16) 7-[4-bis(2-nitrophenyl)methylpiperazino-1-methyl]-2-[(2-hydroxyethyl)amino]-4-isopropyl-2,4,6-cycloheptatrien-1-one
(17) 7-[(4-bis(2-methylphenyl)methylpiperazino-1-methyl]-2-[(2-hydroxyethyl)amino]-4-isopropyl-2,4,6-cycloheptatrien-1-one These compounds can be produced by the method disclosed in JP-A 6-509318 or by a method in accordance therewith.

Now, the compounds of the present invention represented by the general formula (3) are described.

In the compounds of the present invention represented by the general formula (3), the $C_1$ to $C_5$ alkyl group represented by $R_{10}$ includes e.g. methyl, ethyl, n-propyl, isopropyl, n-butyl, isobutyl, n-pentyl, isoamyl, etc., preferably an isopropyl group. The $C_1$ to $C_5$ alkyl group represented by $R_{11}$ includes the same alkyl group as said $R_{10}$. The $C_1$ to $C_5$ alkyl group having a hydroxyl group or an alkoxy group (preferably a $C_1$ to $C_5$ alkoxy group) includes 2-hydroxyethyl, 3-hydroxypropyl methoxymethyl groups and the like. The substituent group on a benzene ring in the benzyl group includes e.g. the above-described $C_1$ to $C_5$ alkyl group, a $C_1$ to $C_5$ halogeno alkyl group such as trifluoromethyl, etc., halogen, nitro group, cyano group or a lower alkoxy group, and these 1 to 4 substituent groups may be contained. Such halogen includes chloro, fluoro, bromo and iodo, and the lower alkoxy group includes a $C_1$ to $C_5$ alkoxy group. The $C_1$ to $C_5$ acyl group includes acetyl, propionyl, butyryl, pivaloyl, etc. $R_{11}$ preferably includes a $C_1$ to $C_5$ alkyl group and a benzyl group unsubstituted or substituted with the above-described substituent group. The $C_1$ to $C_3$ alkyl group represented by $R_{12}$ includes methyl, ethyl, n-propyl and isopropyl, and $R_{12}$ preferably includes a a hydrogen atom atom and a methyl group. The substituent group on a benzene ring in the phenyl, benzyl or benzoyl represented by Z' includes the same substituent groups as on a benzene ring in the benzyl group represented by said $R_{11}$, and this also applies to the substituent group on the 2-pyridyl or 2-pyrimidyl group. Z' preferably includes a phenyl group unsubstituted or substituted with the above-described substituent group. m is preferably the integer of 1, and X is preferably a nitrogen atom.

Examples of the compounds represented by the general formula (3) are shown below:
1) 7-(4-benzylpiperidino-1-methyl)-2-hydroxy-4-isopropyl-2,4,6-cycloheptatrien-1-one
2) 7-(4-benzylpiperidino-1-methyl)-4-isopropyl-2-methoxy-2,4,6-cycloheptatrien-1-one
3) 7-(4-benzylpiperidino-1-methyl)-2-ethoxy-4-isopropyl-2,4,6-cycloheptatrien-1-one
4) 7-(4-benzylpiperidino-1-methyl)-4-isopropyl-2-propoxy-2,4,6-cycloheptatrien-1-one
5) 7-(4-benzylpiperidino-1-methyl)-2-butoxy-4-isopropyl-2,4,6-cycloheptatrien-1-one
6) 2-benzyloxy-7-(4-benzylpiperidino-1-methyl)-4-isopropyl-2,4,6-cycloheptatrien-1-one
7) 7-(4-benzoylpiperidino-1-methyl)-2-hydroxy-4-isopropyl-2,4,6-cycloheptatrien-1-one
8) 7-(4-benzoylpiperidino-1-methyl)-4-isopropyl-2-methoxy-2,4,6-cycloheptatrien-1-one
9) 7-(4-benzoylpiperidino-1-methyl)-2-ethoxy-4-isopropyl-2,4,6-cycloheptatrien-1-one
10) 7-(4-benzoylpiperidino-1-methyl)-4-isopropyl-2-propoxy- 2,4,6-cycloheptatrien-1-one
11) 7-(4-benzoylpiperidino-1-methyl)-2-butoxy-4-isopropyl-2,4,6-cycloheptatrien-1-one
12) 7-(4-benzoylpiperidino-1-methyl)-2-benzyloxy-4-isopropyl-2,4,6-cycloheptatrien-1-one
13) 7-(4-benzylpiperazino-1-methyl)-2-hydroxy-4-isopropyl-2,4,6-cycloheptatrien-1-one
14) 7-(4-benzylpiperazino-1-methyl)-4-isopropyl-2-methoxy-2,4,6-cycloheptatrien-1-one
15) 7-(4-benzylpiperazino-1-methyl)-2-ethoxy-4-isopropyl-2,4,6-cycloheptatrien-1-one
16) 7-(4-benzylpiperazino-1-methyl)-4-isopropyl-2-propoxy-2,4,6-cycloheptatrien-1-one
17) 7-(4-benzylpiperazino-1-methyl)-2-butoxy-4-isopropyl-2,4,6-cycloheptatrien-1-one
18) 2-benzyloxy-7-(4-benzylpiperazino-1-methyl)-4-isopropyl-2,4,6-cycloheptatrien-1-one
19) 2-hydroxy-4-isopropyl-7-(4-phenylpiperazino-1-methyl)-2,4,6-cycloheptatrien-1-one
20) 4-isopropyl-2-methoxy-7-(4-phenylpiperazino-1-methyl)-2,4,6-cycloheptatrien-1-one
21) 2-ethoxy-4-isopropyl-7-(4-phenylpiperazino-1-methyl)-2,4,6-cycloheptatrien-1-one
22) 4-isopropyl-7-(4-phenylpiperazino-1-methyl)-2-propoxy-2,4,6-cycloheptatrien-1-one
23) 2-butoxy-4-isopropyl-7-(4-phenylpiperazino-1-methyl)-2,4,6-cycloheptatrien-1-one
24) 2-benzyloxy-4-isopropyl-7-(4-phenylpiperazino-1-methyl)-2,4,6-cycloheptatrien-1-one
25) 7-[4-(2-chlorophenyl)piperazino-1-methyl]-2-hydroxy-4-isopropyl-2,4,6-cycioheptatrien-1-one
26) 7-[4-(2-chlorophenyl)piperazino-1-methyl]-4-isopropyl-2-methoxy-2,4,6-cycloheptatrien-1-one
27) 7-[4-(2-chlorophenyl)piperazino-1-methyl]-2-ethoxy-4-isopropyl-2,4,6-cycloheptatrien-1-one
28) 7-[4-(2-chlorophenyl)piperazino-1-methyl]-4-isopropyl-2-propoxy-2,4,6-cycloheptatrien-1-one
29) 2-butoxy-7-[4-(2-chlorophenyl)piperazino-1-methyl]-4-isopropyl-2,4,6-cycloheptatrien-1-one
30) 2-benzyloxy-7-[4-(2-chlorophenyl)piperazino-1-methyl]-4-isopropyl-2,4,6-cycloheptatrien-1-one
31) 7-[4-(3-chlorophenyl)piperazino-1-methyl]-2-hydroxy-4-isopropyl-2,4,6-cycloheptatrien-1-one
32) 7-[4-(3-chlorophenyl)piperazino-1-methyl]-4-isopropyl-2-methoxy-2,4,6-cycloheptatrien-1-one
33) 7-[4-(3-chlorophenyl)piperazino-1-methyl)-2-ethoxy-4-isopropyl-2,4,6-cycloheptatrien-1-one
34) 7-[4-(3-chlorophenyl)piperazino-1-methyl]-4-isopropyl-2-propoxy-2,4,6-cycloheptatrien-1-one
35) 2-butoxy-7-[4-(3-chlorophenyl)piperazino-1-methyl)-4-isopropyl-2,4,6-cycloheptatrien-1-one
36) 2-benzyloxy-7-[4-(3-chlorophenyl)piperazino-1-methyl]-4-isopropyl-2,4,6-cycloheptatrien-1-one
37) 7-[4-(3-fluorophenyl)piperazino-1-methyl]-2-hydroxy-4-isopropyl-2,4,6-cycloheptatrien-1-one
38) 7-[4-(3-fluorophenyl)piperazino-1-methyl]-4-isopropyl-2-methoxy-2,4,6-cycloheptatrien-1-one 39) 2-ethoxy-7-[4-(3-fluorophenyl)piperazino-1-methyl]-4-isopropyl-2,4,6-cycloheptatrien-1-one
40) 7-[4-(3-fluorophenyl)piperazino-1-methyl]-4-isopropyl-2-propoxy-2,4,6-cycloheptatrien-1-one
41) 2-butoxy-7-(4-(3-fluorophenyl)piperazino-1-methyl]-4-isopropyl-2,4,6-cycloheptatrien-1-one
42) 2-benzyloxy-7-[4-(3-fluorophenyl)piperazino-1-methyl]-4-isopropyl-2,4,6-cycloheptatrien-1-one
43) 2-hydroxy-4-isopropyl-7-[4-(4-methylphenyl)piperazino-1-methyl]-2,4,6-cycloheptatrien-1-one
44) 4-isopropyl-2-methoxy-7-[4-(4-methylphenyl)piperazino-1-methyl]-2,4,6-cycloheptatrien-1-one
45) 2-ethoxy-4-isopropyl-7-[4-(4-methylphenyl)piperazino-1-methyl]-2,4,6-cycloheptatrien-1-one
46) 4-isopropyl-7-[4-(4-methylphenyl)piperazino-1-methyl]-2-propoxy-2,4,6-cycloheptatrien-1-one
47) 2-butoxy-4-isopropyl-7-[4-(4-methylphenyl)piperazino-1-methyl]-2,4,6-cycloheptatrien-1-one
48) 2-benzyloxy-4-isopropyl-7-[4-(4-methylphenyl)piperazino-1-methyl]-2,4,6-cycloheptatrien-1-one
49) 2-hydroxy-4-isopropyl-7-[4-(3-methylphenyl)piperazino-1-methyl]-2,4,6-cycloheptatrien-1-one
50) 4-isopropyl-2-methoxy-7-[4-(3-methylphenyl)piperazino-1-methyl]-2,4,6-cycloheptiatrieti-1-one
51) 2-ethoxy-4-isopropyl-7-[4-(3-methylphenyl)piperazino-1-methyl]-2,4,6-cycloheptatrien-1-one
52) 4-isopropyl-7-[4-(3-methylphenyl)piperazino-1-methyl]-2-propoxy-2,4,6-cycloheptatrien-1-one
53) 2-butoxy-4-isopropyl-7-[4-(3-methylphenyl)piperazino-1-methyl]-2,4,6-cycloheptatrien-1-one
54) 2-benzyloxy-4-isopropyl-7-[4-(3-methylphenyl)piperazino-1-methyl]-2,4,6-cycloheptatrien-1-one
55) 2-hydroxy-4-isopropyl-7-[4-(2-methoxyphenyl)piperazino-1-methyl]-2,4,6-cycloheptatrien-1-one
56) 4-isopropyl-2-methoxy-7-[4-(2-methoxyphenyl)piperazino-1-methyl]-2,4,6-cycloheptatrien-1-one
57) 2-ethoxy-isopropyl-7-[4-(2-methoxyphenyl)piperazino-1-methyl]-2,4,6-cycloheptatrien-1-one
58) 4-isopropyl-7-[4-(2-methoxyphenyl)piperazino-1-methyl]-2-propoxy-2,4,6-cycloheptatrien-1-one
59) 2-butoxy-4-isopropyl-7-[4-(2-methoxyphenyl)piperazino-1-methyl]-2,4,6-cycloheptatrien-1-one
60) 2-benzyloxy-4-isopropyl-7-[4-(2-methoxyphenyl)piperazino-1-methyl]-2,4,6-cycloheptatrien-1-one
61) 2-hydroxy-4-isopropyl-7-[4-(4-methoxyphenyl)piperazino-1-methyl]-2,4,6-cycloheptatrien-1-one
62) 4-isopropyl-2-methoxy-7-[4-(4-methoxyphenyl)piperazino-1-methyl]-2,4,6-cycloheptatrien-1-one
63) 2-ethoxy-isopropyl-7-8-(4-methoxyphenyl)piperazino-1-methyl]-2,4,6-cycloheptatrien-1-one
64) 4-isopropyl-7-[4-(4-methoxyphenyl)piperazino-1-methyl]-2-propoxy-2,4,6-cycloheptatrien-1-one
65) 2-butoxy-4-isopropyl-7-[4-(4-methoxyphenyl)piperazino-1-methyl]-2,4,6-cycloheptatrien-1-one
66) 2-benzyloxy-4-isopropyl-7-[4-(4-methoxyphenyl)piperazino-1-methyl]-2,4,6-cycloheptatrien-1-one
67) 2-hydroxy-4-isopropyl-7-[4-(4-nitrophenyl)piperazino-1-methyl]-2,4,6-cycloheptatrien-1-one
68) 4-isopropyl-2-methoxy-7-[4-(4-nitrophenyl)piperazino-1-methyl]-2,4,6-cycloheptatrien-1-one
69) 2-ethoxy-4-isopropyl-7-[4-(4-nitrophenyl)piperazino-1-methyl]-2,4,6-cycloheptatrien-1-one
70) 4-isopropyl-7-[4-(4-nitrophenyl)piperazino-1-methyl]-2-propoxy-2,4,6-cycloheptatrien-1-one
71) 2-butoxy-4-isopropyl-7-[4-(4-nitrophenyl)piperazino-1-methyl]-2,4,6-cycloheptatrien-1-one
72) 2-benzyloxy-4-isopropyl-7-[4-(4-nitrophenyl)piperazino-1-methyl]-2,4,6-cycloheptatrien-1-one
73) 2-hydroxy-4-isopropyl-7-[4-(2-methylthiophenyl)piperazino-1-methyl]-2,4,6-cycloheptatrien-1-one
74) 4-isopropyl-2-methoxy-7-[4-(2-methylthiophenyl)piperazino-1-methyl]-2,4,6-cycloheptatrien-1-one
75) 2-ethoxy-4-isopropyl-7-[4-(2-methylthiophenyl)piperazino-1-methyl]-2,4,6-cycloheptatrien-1-one
76) 4-isopropyl-7-[4-(2-methylthiophenyl)piperazino-1-methyl]-2-propoxy-2,4,6-cycloheptatrien-1-one
77) 2-butoxy-4-isopropyl-7-[4-(2-methylthiophenyl)piperazino-1-methyl]-2,4,6-cycloheptatrien-1-one
78) 2-benzyloxy-4-isopropyl-7-[4-(2-methylthiophenyl)piperazino-1-methyl]-2,4,6-cycloheptatrien-1-one
79) 7-[4-(2,4-dimethylphenyl)piperazino-1-methyl]-2-hydroxy-4-isopropyl-2,4,6-cycloheptatrien-1-one
80) 7-[4-(2,4-dimethylphenyl)piperazino-1-methyl]-4-isopropyl-2-methoxy-2,4,6-cycloheptatrien-1-one
81) 7-14-(2,4-dimethylphenyl)piperazino-1-methyl]-2-ethoxy-4-isopropyl-2,4,6-cycloheptatrien-1-one
82) 7-[4-(2,4-dimethylphenyl)piperazino-1-methyl]-4-isopropyl-2-propoxy-2,4,6-cycloheptatrien-1-one
83) 2-butoxy-7-[4-(2,4-dimethylphenyl)piperazino-1-methyl]-4-isopropyl-2,4,6-cycloheptatrien-1-one
84) 2-benzyloxy-7-[4-(2,4-dimethylphenyl)piperazino-1-methyl]-4-isopropyl-2,4,6-cycloheptatrien-1-one
85) 2-hydroxy-4-isopropyl-7-(3-methyl-4-phenylpiperazino- 1-methyl)-2,4,6-cycloheptatrien-1-one
86) 4-isopropyl-2-methoxy-7-(3-methyl-4-phenylpiperazino-1-methyl)-2,4,6-cycloheptatrien-1-one
87) 2-ethoxy-4-isopropyl-7-(3-methyl-4-phenylpiperazino-1-methyl)-2,4,6-cycloheptatrien-1-one
88) 4-isopropyl-7-(3-methyl-4-phenylpiperazino-1-methyl)-2-propoxy-2,4,6-cycloheptatrien-1-one
89) 2-butoxy-4-isopropyl-7-(3-methyl-4-phenylpiperazino-1-methyl)-2,4,6-cycloheptatrien-1-one
90) 2-benzyloxy-4-isopropyl-7-(3-methyl-4-phenylpiperazino-1-methyl)-2,4,6-cycloheptatrien-1-one
91) 2-benzyloxy-7-[4-(4-fluorophenyl)piperazino-1-methyl]-4-isopropyl-2,4,6-cycloheptatrien-1-one
92) 2-ethoxy-7-[4-(4-fluorophenyl)piperazino-1-methyl]-4-isopropyl-2,4,6-cycloheptatrien-1-one
93) 7-[4-(4-fluorophenyl)piperazino-1-methyl]-2-hydroxy-4-isopropyl-2,4,6-cycloheptatrien-1-one Pharmaceutically acceptable salts of these compounds include salts with the above-described acids.

When a pharmaceutically acceptable salt of the tropone derivative of the invention represented by the general formula (3) is used as a pharmaceutical preparation such as a therapeutic agent for pollakiuria and urinary incontinence, said compound is used usually in a pharmaceutical composition comprising pharmaceutically acceptable additives (excipients, carriers, diluent etc.). The content of the tropone derivative of the invention or its salt in the composition is usually 0.01 to 99.5% by weight, preferably 0.1 to 90% by weight, the remainder being pharmaceutical additives. The administration route, dosage etc. are as described in the general description.

The tropone derivative shown in the general formula (3) is a novel compound and can be produced as described below. The production route of the compound of the general formula (3) is shown below.

Production route of the compound of the general formula (3)

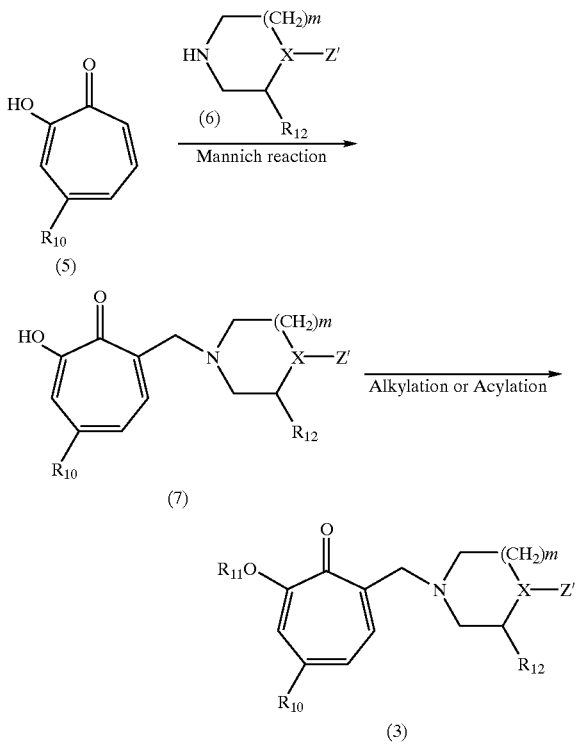

(In the reaction scheme, $R_{10}$, $R_{11}$, $R_{12}$, Z', X and m have the same meanings as described above.)

[Reaction 1]

The substituted tropone derivative of the general formula (7) can be produced by subjecting the tropone compound of the general formula (5) and the heterocyclic compound of the general formula (6) to Mannich reaction.

The tropone compound of the general formula (5) includes hinokitiol (2-hydroxy-4-isopropyl-2,4,6-cycloheptatrien-1-one) etc. The heterocyclic compound of the general formula (6) includes 1-phenylpiperazine, 1-(4-chloro-2-methylphenyl)piperazine, 1-(5-chloro-2-methylphenyl)piperazine, 1-(4-chlorophenyl)piperazine, 1-(4-bromophenyl)piperazine, 1-(4-fluorophenyl)piperazine, 1-(3-fluorophenyl)piperazine, 1-(2-methylphenyl)piperazine, 1-(3-methylphenyl)piperazine, 1-(4-methylphenyl)piperazine, 1-(2,5-dimethylphenyl)piperazine, 1-(4-chloromethylphenyl)piperazine, 1-(2-ethylphenyl)piperazine, 1-(4-propylphenyl)piperazine, 1-(2-methoxyphenyl)piperazine, 1-(3-methoxyphenyl)piperazine, 1-(4-methoxyphenyl)piperazine, 1-(3-methylthiophenyl)piperazine, 1-(4-nitrophenyl)piperazine, 1-(4-cyanophenyl)piperazine, 1-(2-pyridyl) piperazine, 1-benzylpiperazine, 1-benzyl-2-methyl piperazine, 4-benzylpiperazine, 1-benzoylpiperazine and 1-(2-pyrimidyl)piperazine.

The amount of the heterocyclic compound of the general formula (6) is 0.5 to 10 equivalents, preferably 0.8 to 2 equivalents, more preferably 1 to 1.2 equivalents, relative to the tropone compound of the general formula (5), and the aqueous formalin solution is used in an amount of 0.5 to 30 equivalents, preferably 0.8 to 2 equivalents. The reaction solvent includes, but is not limited to, alcohols (methanol, ethanol, propanol etc.), esters (methyl acetate, ethyl acetate etc.), ethers (ethyl ether, isopropyl ether, tetrahydrofuran, dioxane etc.), aromatic hydrocarbons (benzene, toluene, xylene etc.), aliphatic hydrocarbons (pentane, hexane etc.), water and acetic acid, and preferably alcohols are used. The acid includes mineral acids such as hydrochloric acid, sulfuric acid, etc. and organic acids such as p-toluenesulfonic acid, acetic acid, etc. and acetic acid is preferably used. The amount of the acid used is from 0.01 equivalent to the amount of solvent, preferably 1 to 2 equivalents. The reaction temperature is in the vicinity of −10° C. to the boiling point of solvent, and preferably in the vicinity of room temperature to the boiling point of solvent, and the reaction time is 0.5 to 24 hours, and preferably 2 to 8 hours. In treatment after the reaction, the desired compound of the general formula (7) can be produced by general purification techniques, such as the cooling the reaction solution to precipitate crystals followed by filtration, or concentration followed by recrystallization or column chromatography, etc.

[Reaction 2-A]

Alkylation of a hydroxyl group in the substituted tropone derivative of the general formula (7) is conducted in an organic solvent by adding a basic catalyst and an alkylating agent. The basic catalyst includes sodium carbonate, potassium carbonate, sodium hydroxide, potassium hydroxide, sodium hydride, triethylamine, pyridine, etc. and the amount of the catalyst used is 0.5 to 10 equivalents, and preferably 0.8 to 2 equivalents, and the alkylating agent includes alkyl halides (methyl iodide, ethyl bromide, butyl bromide, benzyl bromide etc.), dimethyl sulfate, diethyl sulfate etc., and its amount for use is 0.5 to 10 equivalents, and preferably 0.8 to 3 equivalents. The reaction solvent includes, but is not limited to, ketones (acetone, methyl ethyl ketone, methyl isobutyl ketone etc.), esters (methyl acetate, ethyl acetate etc.), ethers (ethyl ether, isopropyl ether, tetrahydrofuran, dioxane etc.), aromatic hydrocarbons (benzene, toluene, xylene etc.), aliphatic hydrocarbons (pentane, hexane etc.), halogen-type solvents (methylene chloride, chloroform, 1,2-dichloroethane etc.) etc.

Preferably, the reaction temperature is in the vicinity of −10° C. to the boiling point of solvent and the reaction time is 0.5 to 48 hours. In treatment after the reaction, the desired product can be produced by general purification techniques such as recrystallization, column chromatography or the like.

[Reaction 2-B]

Acylation of a hydroxyl group in the substituted tropone derivative of the general formula (7) is conducted in an organic solvent by adding a basic catalyst and an acylating agent.

The basic catalyst includes sodium carbonate, potassium carbonate, triethylamine, pyridine etc., and the amount of the catalyst is 0.5 to 10 equivalents, and preferably 0.8 to 2 equivalents. The acylating agent includes acid anhydrides (acetic anhydride, trifluoroacetic anhydride etc.), acid halides (acetyl chloride, butyryl chloride, benzoyl chloride etc.) etc., and its amount for use is 0.5 to 10 equivalents, and preferably 0.8 to 2 equivalents. The reaction is carried out with or without organic solvent. The reaction solvent includes, but is not limited to, ethers (ethyl ether, isopropyl ether, tetrahydrofuran, dioxane etc.), aromatic hydrocarbons (benzene, toluene, xylene etc.), aliphatic hydrocarbons (pentane, hexane etc.), halogen-type solvents (methylene chloride, chloroform, 1,2-dichloroethane etc.) etc. Preferably, the reaction temperature is in the vicinity of −10° C. to the boiling point of solvent and the reaction time is 0.5 to 48 hours. In treatment after the reaction, the desired product can be produced by general purification techniques such as recrystallization, column chromatography or the like.

Now, the compounds represented by the general formula (4) are described.

In the compounds of the invention represented by the general formula (4), the $C_1$ to $C_5$ alkyl group represented by $R_{10}$ includes e.g. methyl, ethyl, n-propyl, isopropyl, n-butyl, isobutyl, n-pentyl, isoamyl, etc., preferably an isopropyl group. $R_7$ and $R_8$ are the same or different and include a hydrogen atom or $C_1$ to $C_{10}$ lower alkyl groups such as methyl, ethyl, propyl, isopropyl, etc., substituted $C_1$ to $C_5$ lower alkyl groups such as 2-hydroxyethyl, 3-hydroxypropyl, 2-[N,N-dimethylamino] ethyl, 3-[N,N-dimethylamino]propyl, etc., substituted or unsubstituted aralkyl groups such as benzyl, phenethyl, etc. (the number of carbon atoms in the aralkyl group is preferably 7 to 20). The substituent group on an aromatic ring in the aralkyl group includes the same $C_1$ to $C_5$ alkyl group as said $R_{10}$, halogen such as chlorine atom, fluorine atom and bromine atom, nitro group, cyano group or $C_1$ to $C_5$ lower alkoxy group, and these 1 to 4 substituent groups may be contained. Further, when $R_7$ and $R_8$ are combined to form a hetero ring, —$NR_7R_8$ includes 5- to 10-membered, preferably 5- to 7-membered heterocyclic group, such as pyrrolidino, piperazino, piperidino, morpholino, etc. and it may have 1 to 4 substituent groups, in which the same $C_1$ to $C_5$ alkyl group as $R_{10}$, nitro group, cyano group or $C_1$ to $C_5$ lower alkoxy group etc. A preferable combination of $R_7$ and $R_8$ includes a combination of a hydrogen atom or a methyl group and a hydroxy-containing $C_1$ to $C_5$ alkyl group such as 2-hydroxymethyl or 3-hydroxypropyl etc. $R_{12}$ includes a hydrogen atom or $C_1$ to $C_3$ alkyl groups such as methyl, ethyl, n-propyl, isopropyl, etc. and a hydrogen atom and a methyl group are preferable. $R_9$ includes a hydrogen atom or the same $C_1$ to $C_5$ alkyl groups as said $R_{10}$, or an aromatic group which may be substituted with 1 to 4 groups selected from halogens such as chlorine atom, fluorine atom and bromine atom, nitro groups, cyano groups and $C_1$ to $C_5$ lower alkoxy groups (the number of carbon atoms in said aromatic group is 6 to 10, such as phenyl and naphthyl groups). The substituent group on a benzene ring in the phenyl, benzyl or benzoyl represented by Z' includes the same substituent groups as on a benzene ring in the aralkyl group represented by said $R_7$ or $R_8$, and this also applies to the substituent group on the 2-pyridyl or 2-pyrimidyl group. Z' preferably includes a phenyl group unsubstituted or substituted with the above-described substituent group. m is preferably the integer of 1, and X is preferably a nitrogen atom.

Examples of the compounds represented by the general formula (4) include the following compounds:

1) 4-isopropyl-2-methylamino-7-(4-phenylpiperazino-1-methyl)-2,4,6-cycloheptatrien-1-one
2) 2-ethylamino-4-isopropyl-7-(4-phenylpiperazino-1-methyl)-2,4,6-cycloheptatrien-1-one
3) 4-isopropyl-7-(4-phenylpiperazino-1-methyl)-2-propylamino-2,4,6-cycloheptatrien-1-one
4) 4-isopropyl-2-isopropylamino-7-(4-phenylpiperazino-1-methyl)-2,4,6-cycloheptatrien-1-one
5) 2-butylamino-4-isopropyl-7-(4-phenylpiperazino-1-methyl)-2,4,6-cycloheptatrien-1-one
6) 2-benzylamino-4-isopropyl-7-(4-phenylpiperazino-1-methyl)-2,4,6-cycloheptatrien-1-one
7) 2-dimethylamino-4-isopropyl-7-(4-phenylpiperazino-1-methyl)-2,4,6-cycloheptatrien-1-one
8) 2-diethylamino-4-isopropyl-7-(4-phenylpiperazino-1-methyl)-2,4,6-cycloheptatrien-1-one
9) 2-diisopropylamino-4-isopropyl-7-(4-phenylpiperazino-1-methyl)-2,4,6-cycloheptatrien-1-one
10) 4-isopropyl-7-(4-phenylpiperazino-1-methyl)-2-piperidino-2,4,6-cycloheptatrien-1-one
11) 4-isopropyl-7-(4-phenylpiperazino-1-methyl)-2-pyrrolidino-2,4,6-cycloheptatrien-1-one
12) 4-isopropyl-2-(4-methylpiperidino)-7-(4-phenylpiperazino-1-methyl)-2,4,6-cycloheptatrien-1-one
13) 4-isopropyl-7-(4-phenylpiperazino-1-methyl)-2-piperazino-2,4,6-cycloheptatrien-1-one
14) 4-isopropyl-2-(4-methylpiperazino)-7-(4-phenylpiperazino-1-methyl)-2,4,6-cycloheptatrien-1-one
15) 4-isopropyl-2-morpholino-7-(4-phenylpiperazino-1-methyl)-2,4,6-cycloheptatrien-1-one
16) 7-[4-(4-fluorophenyl)piperazino-1-methyl]-2-[(2-hydroxyethyl)amino]-4-isopropyl-2,4,6-cycloheptatrien-1-one
17) 2-[(2-hydroxyethyl)methylamino]-4-isopropyl-7-(4-phenylpiperazino-1-methyl)-2,4,6-cycloheptatrien-1-one
18) 2-[(2-hydroxypropyl)amino]-4-isopropyl-7-(4-phenylpiperazino-1-methyl)-2,4,6-cycloheptatrien-1-one
19) 2-[(2-hydroxyethoxy)ethylamino]-4-isopropyl-7-(4-phenylpiperazino-1-methyl)-2,4,6-cycloheptatrien-1-one
20) 4-isopropyl-2-[(2-methoxyethyl)amino]-7-(4-phenylpiperazino-1-methyl)-2,4,6-cycloheptatrien-1-one
21) 7-[4-(4-chloro-2-methylphenyl)piperazino-1-methyl]-2-[(2-hydroxyethyl)amino]-4-isopropyl-2,4,6-cycloheptatrien-1-one Pharmaceutically acceptable salts of the tropone derivative of the invention represented by the general formula (4) include salts with mineral acids such as hydrochloric acid and sulfuric acid, etc. salts with organic sulfonic acids such as methanesulfonic acid and p-toluenesulfonic acid, etc. as well as salts with organic carboxylic acid such as acetic acid, propionic acid, succinic acid, lactic acid, tartaric acid and malic acid, etc.

When a pharmaceutically acceptable salt of the tropone derivative of the invention represented by the general formula (4) is used as a pharmaceutical preparation such as a therapeutic agent for pollakiuria and urinary incontinence, said compound is used usually as a pharmaceutical composition comprising the said compound and pharmaceutically acceptable additives (excipients, carriers, diluent etc.). The content of the tropone derivative of the invention or its salt in the composition is usually 0.01 to 99.5% by weight, preferably 0.1 to 90% by weight, the remainder being pharmaceutical additives. The pharmaceutical preparation can be administered via a suitable route including oral, rectal, nasal, topical (including buccal and sublingual), vaginal, bladder, parenteral (including subcutaneous, intramuscular, intravenous and cutaneous) and percutaneous (ointment, cream, paste etc.) routes. A preferable route is determined depending on the condition and age of a patient and the actual condition to be treated. The dosage is varied depending on the administration route, the age of a patient and the actual condition to be treated, and for example in the case of oral administration into an adult person, 0.1 mg to 2000 mg, preferably 1 mg to 100 mg of the active ingredient can be administered daily once or several times in portions.

The tropone derivative of the general formula (4) is a novel compound and can be produced in the following manner. The production route of the compound of the general formula (4) is shown below.

Production route of the compound of the general formula (4)

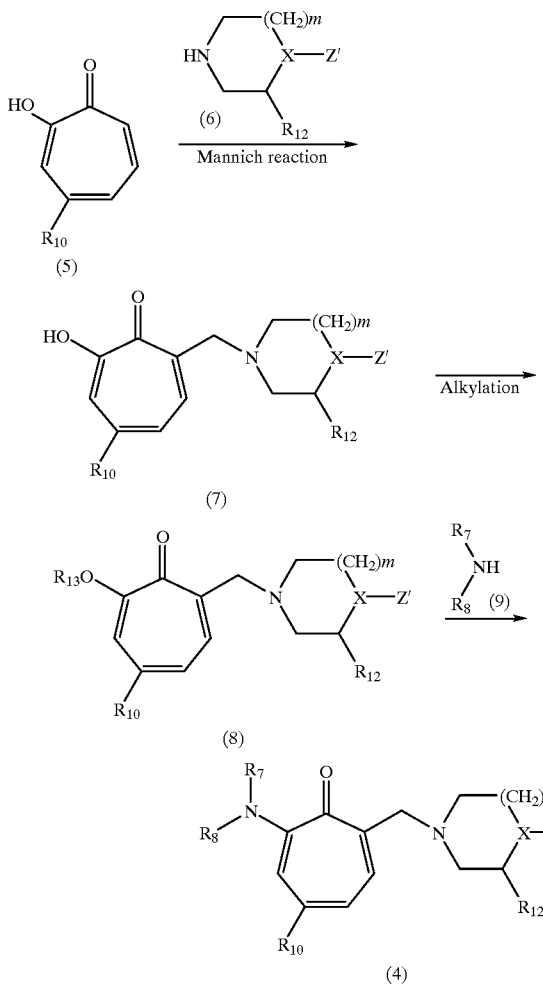

(In the reaction scheme, $R_7$, $R_8$, $R_{10}$, $R_{12}$, Z', X and m have the same meanings as defined above. $R_{13}$ represents $C_1$ to $C_5$ alkyl groups.)

[Reaction 1]

The substituted tropone derivative of the general formula (7) can be produced by subjecting the tropone compound of the general formula [5] and the heterocyclic compound of the general formula [6] to Mannich reaction.

The amount of the heterocyclic compound of the general formula (6) is 0.5 to 10 equivalents, preferably 0.8 to 2 equivalents, more preferably 1 to 1.2 equivalents, relative to the tropone compound of the general formula (5), and the aqueous formalin solution is used in an amount of 0.5 to 30 equivalents, preferably 0.8 to 2 equivalents. The reaction solvent includes, but is not limited to, alcohols (methanol, ethanol, propanol etc.), esters (methyl acetate, ethyl acetate etc.), ethers (ethyl ether, isopropyl ether, tetrahydrofuran, dioxane etc.), aromatic hydrocarbons (benzene, toluene, xylene etc.) aliphatic hydrocarbons (pentane, hexane etc.), water and acetic acid, etc. and preferably alcohols are used. The acid includes mineral acids such as hydrochloric acid and sulfuric acid, etc. and organic acids such as p-toluenesulfonic acid and acetic acid, etc. and acetic acid is preferably used. The amount of the acid used is from 0.01 equivalent to the amount of solvent, preferably 1 to 2 equivalents. The reaction temperature is in the vicinity of −10° C. to the boiling point of solvent, and preferably in the vicinity of room temperature to the boiling point of solvent, and the reaction time is 0.5 to 24 hours, and preferably 2 to 8 hours. In treatment after the reaction, the desired compound of the general formula (7) can be produced by general purification techniques, such as the cooling the reaction solution to precipitate crystals followed by filtration, or concentration followed by recrystallization or column chromatography, etc.

[Reaction 2]

Alkylation of a hydroxyl group in the substituted tropone derivative of the general formula (7) is conducted in an organic solvent by adding a basic catalyst and an alkylating agent. The basic catalyst includes sodium carbonate, potassium carbonate, sodium hydroxide, potassium hydroxide, sodium hydride, triethylamine, pyridine etc., and its amount for use is 0.5 to 10 equivalents, preferably 0.8 to 2 equivalents, relative to the substituted tropone derivative of the general formula (7). The alkylating agent includes alkyl halides (methyl iodide, ethyl bromide, butyl bromide etc.), dimethyl sulfate, diethyl sulfate etc., and its amount for use is 0.5 to 10 equivalents, preferably 0.8 to 3 equivalents. The reaction solvent includes, but is not limited to, ketones (acetone, methyl ethyl ketone, methyl isobutyl ketone etc.), esters (methyl acetate, ethyl acetate etc.), ethers (ethyl ether, isopropyl ether, tetrahydrofuran, dioxane etc.), aromatic hydrocarbons (benzene, toluene, xylene etc.), aliphatic hydrocarbons (pentane, hexane etc.), halogen-type solvents (methylene chloride, chloroform, 1,2-dichloroethane etc.) etc. The reaction temperature is in the vicinity of −10° C. to the boiling point of solvent, preferably in the vicinity of room temperature to the boiling point of solvent, and the reaction time is preferably 0.5 to 48 hours. In treatment after the reaction, the compound of the general formula (8) can be produced by general purification techniques such as recrystallization or column chromatography.

[Reaction 3]

The compound of the general formula (4) can be produced by converting the compound (8) by amine (9). The amine (9) includes e.g. morpholine, piperidine, N-methylpiperazine, N-phenylpiperazine, N-p-chlorophenylpiperazine, methylamine, dimethylamine, ethylamine, propylamine, 2-hydroxyethylamine, 2-hydroxypropylamine, 3-hydroxypropylamine, benzylamine and p-methylbenzylamine, etc. The amount of amine (9) used is 0.5 to 30 equivalents, preferably 0.8 to 30 equivalents, relative to the tropone compound, and the reaction solvent includes, but is not limited to, alcohols (methanol, ethanol, propanol etc.), esters (methyl acetate, ethyl acetate etc.), ethers (ethyl ether, isopropyl etlier, tetrahydrofuratn, dioxane etc.), aromatic hydrocarbons (benzene, toluene, xylene etc.), aliphatic hydrocarbons (pentane, hexane etc.), water or the like. Further, the desired compound can also be produced by use of excessive amines even in the absence of solvent. The reaction temperature is in the vicinity of −10° C. to the boiling point of solvent, and preferably in the vicinity of room temperature to the boiling point of solvent, and the reaction time is 0.5 to 24 hours, preferably 1 to 8 hours. In treatment after the reaction, the desired compound of the general formula (7) can be produced by general purification techniques, such as the cooling the reaction solution to precipitate crystals followed by filtration, or concentration followed by recrystallization or column chromatography, etc.

The compound having a tropone structure or its pharmaceutically acceptable salt can be combined as necessary with pharmaceutically acceptable carries, excipients and diluent to prepare powder, granules, tablets, capsules and injections, etc. The amount of the compound having a tropone structure or its pharmaceutically acceptable salt in the pharmaceutical preparation is preferably in the range of 0.01 to 100% by weight. The pharmaceutical preparation can be administered through a suitable route including oral, rectal, nasal, topical (including buccal and sublingual), vaginal, bladder, parenteral (including subcutaneous, intramuscular, intravenous and cutaneous) and percutaneous (ointment, cream, paste etc.) routes. A preferable route is determined depending on the condition and age of a patient and the actual condition to be treated. The dosage is varied depending on the administration route, the age of a patient and the actual condition to be treated, and for example in the case of oral administration into an adult person, 0.1 mg to 2000 mg, preferably 1 mg to 100 mg of the active ingredient can be administered daily once or several times in portions.

Present invention will be described in more detail by way of tests and examples.

Test

Micturition reflex inhibitory effects of the compounds having the tropon structure according to the present invention was demonstrated by the effects on the rhythmic bladder contraction using the modification of the Kaseda's method (*RINSHO SEIRI* 5, 540–547(1975)).

Method

The Effects on the Rhythmic Bladder Contraction Effect in Rat:

A male Wistar male rat anesthetized with intraperitoneal administration of urethane (1 g/Kg) was subjected to amidoline abdominal incision to expose the bladder, whose dome was cut to make a small opening for inserting a polyethylene tube catheter before ligation. The other end of the catheter was connected to a pressure transducer to measure intravesical pressure. The rat was left for a small period with the urethra ligated. Warmed physiological saline was injected into the bladder through a catheter inserted in the bladder side of an ureter to induce rhythmic bladder contraction. Then change in the intravesical pressure was depicted on a recorder through the pressure transducer. A drug was administered in the common cervical vein by 5 mg/Kg. The drug effect was expressed as prolongation coefficient in rhythmic bladder contraction.

Prolongation Coefficient=[maximum contraction interval after administration]/[mean contraction interval for 10 min before administration].

The below sample drugs represented by the general formula (2) of the present invention were assessed by the above evaluation method. Flavoxate hydrochloride (FRA) and propiverine hydrochloride (PRO), the current remedies for pollakiuria and urinary incontinence were used for reference drugs. The assessment is shown in Table 1.

Sample drug 1: 7-[4-(diphenylmethyl)piperazino-1-methyl]-2-[(2-hydroxyethyl)amino]-4-isopropyl-2,4,6-cycloheptatrien-1-one hydrochloride Sample drug 2: 7-[4-bis(4-fluorophenyl)metlhylpiperazino-1-methyl]-2-[(2-hydroxyethyl)amino]-4-isopropyl-2,4,6-cycloheptatrien-1-one hydrochloride

TABLE 1

Rhythmic bladder contraction effect in rat (5 mg/Kg i.v.)

| Drug | Prolongation coefficient (±S.E.) |
|---|---|
| Reference drug FRA | 4.73 ± 0.88 (n = 6) |
| Reference drug PRO | 6.86 ± 1.53 (n = 6) |
| Sample drug 1 | 14.46 ± 4.65 (n = 3) |
| Sample drug 2 | 6.88 (n = 2) |

Test 2

The below compounds represented by the general formula (3) of the present invention obtained in Example 1, 19, 20, 21 and 23 were assessed by the above evaluation method. Flavoxate hydrochloride (FRA) and propiverine hydrochloride (PRO), the current remedies for pollakiuria and urinary incontinence were used for reference drugs. The assessment is shown in Table 2.

The Example 1 compound: 2-hydroxy-4-isopropyl-7-(4-phenyl piperazino-1-methyl)-2,4,6-cycloheptatrien-1-one;

The Example 19 compound: 2-ethoxy-4-isopropyl-7-(4-phenyl piperazino-1-methyl)-2,4,6-cycloheptatrien-1-one;

The Example 20 compound: 7-[4-(4-chloro-2-methylphenyl)piperazino-1-methyl]-2-ethoxy-4-isopropyl-2,4,6-cycloheptatrien-1-one;

The Example 21 compound: 2-ethoxy-4-isopropyl-7-[4-(4-nitrophenyl)piperazino-1-methyl)-2,4,6-cycloheptatrien-1-one;

The Example 23 compound: 2-benzyloxy-4-isopropyl-7-(4-phenyl piperazino-1-methyl)-2,4,6-cycloheptatrien-1-one;

TABLE 2

Rhythmic bladder contraction effect in rat (5 mg/Kg i.v.)

| Drug | Prolongation Coefficient (±S.E.) |
|---|---|
| Example 1 compound | 12.72 ± 5.97 (n = 3) |
| Example 19 compound | 22.25 ± 1.98 (n = 3) |
| Example 20 compound | 9.23 ± 3.87 (n = 3) |
| Example 21 compound | 11.70 ± 2.77 (n = 3) |
| Example 23 compound | 14.24 ± 4.23 (n = 3) |
| Reference drug (PRO) | 6.86 ± 1.53 (n = 6) |
| Reference drug (FRA) | 4.73 ± 0.88 (n = 6) |

Test 3

The below compounds represented by the general formula (4) of the present invention obtained in Example 26, 27 and 36 were assessed by the above evaluation method. Flavoxate hydrochloride (FRA) and propiverine hydrochloride (PRO), the current remedies for pollakiuria and urinary incontinence were used for reference drugs. The assessment is shown in Table 3.

The Example 26 compound: 4-isoproppyl-7-(4-phenylpiperazino-1-methyl)-2-piperizino-2,4,6-cycloheptatrien-1-one;

The Example 27 compound: 2-[(2-hydroxyethyl)amino]-4-isoprofyl-7-(4-phenylpiperazino-1-methyl)-2,4,6-cycloheptatrien-1-one;

The Example 36 compound: 7-[4-(4-chloro-2-methylphenyl)piperazino-1-methyl]-2-[(2-hydroxyethyl)amino]-4-isopropyl-2,4,6-cycloheptatriene-1-one

TABLE 3

Rhythmic bladder contraction effect in rat (5 mg/Kg i.v.)

| Drug | Prolongation coefficient (±S.E.) |
|---|---|
| Example 26 compound | 6.78 ± 0.62 (n = 3) |
| Example 27 compound | 10.17 ± 4.24 (n = 3) |
| Example 36 compound | 17.05 ± 7.18 (n = 3) |
| Reference drug (PRO) | 6.86 ± 1.53 (n = 6) |
| Reference drug (FRA) | 4.73 ± 0.88 (n = 6) |

EXAMPLE 1

Production of 2-hydroxy-4-isopropyl-7-(4-phenylpiperazino-1-methyl)-2,4,6-cycloheptatrien-1-one To hinokitiol (8.2 g, 50 mmol), 1-phenylpiperazine (7.8 ml, 50 mmol) and acetic acid (2.9 ml 50 mmol) dissolved in methanol 5 ml was added 37% aqueous formalin solution (4.1 ml, 50 mmol) before heating at 60° C. for 2.5 hrs. Ice-cooling, then precipitated crystal, was separated by filtration to give 2-hydroxy-4-isopropyl-7-(4-phenylpiperazino-1-methyl)-2,4,6-cycloheptatrien-1-one (12.2 g, 36 mmol, 72%).

MS (m/z): 339 (M+H)$^+$; $^1$H-NMR (CD$_3$OD) δ (ppm): 1.28 (6H, d, J=6.9 Hz), 2.82 (4 H, t, J=5.0 Hz), 2.93 (1 H, qui, J=6.9 Hz), 3.24 (4 H, t, J=5.0 Hz), 3.86 (2 H, s), 6.79–6.89 (1 H, m), 6.93–7.07 (3 H), 7.18–7.32 (3 H), 7.74 (1 H, d, J=10.6 Hz).

EXAMPLE 2

Production of 7-[4-(2-chlorophenyl)piperazino-1-methyl]-2-hydroxy-4-isopropyl-2,4,6-cycloheptatrien-1-one To hinokitiol (300 mg, 1.83 mmol), 1-(2-chlorophenyl)piperazine dihydrochloride (493 mg, 1.83 mmol), acetic acid (105 µl, 1.83 mmol) and potassium carbonate (506 mg, 3.66 mmol) dissolved in methanol 5 ml was added 37% aqueous formalin solution (188 µl, 2.32 mmol) before heating at 60° C. for 2.5 hrs. The solution was concentrated under reduced pressure to give a residue, to which methylene chloride was added, then the resultant solution was washed with water. The organic layer was dried over magnesium sulfate, and concentrated under reduced pressure to give a residue, which was purified by silica gel chromatography[elution solvent: methylene chloride-methanol-acetic acid (100:5:1)] to obtain 7-[4-(2-chlorophenyl)piperazino-1-methyl]-2-hydroxy-4-isopropyl-2,4,6-cycloheptatrien-1-one (251 mg, 0.67 mmol, 37%).

MS (m/z): 373 (M+H)$^+$; $^1$H-NMR (CDCl$_3$) δ (ppm): 1.29 (6 H, d, J=6.8 Hz), 2.75 (4 H, t, J=4.8 Hz), 2.91 (1 H, qui, J=6.9 Hz), 3.12 (4 H, t, J=4.7 Hz), 3.79 (2 H, s), 6.92–7.08 (3 H), 7.22 (1 H, m), 7.30–7.38 (2 H), 7.80 (1 H, d, J=10.6 Hz).

EXAMPLE 3

Production of 7-[4-(3-chlorophenyl)piperazino-1-methyl]-2-hydroxy-4-isopropyl-2,4,6-cycloheptatrien-1-one The same process using hinokitiol (300 mg, 1.83 mmol) and 1-(3-chlorophenyl)piperazine dihydrochloride (493 mg, 1.83 mmol) as carried out in Example 2 produced 7-[4-(3-chlorophenyl)piperazino-1-methyl]-2-hydroxy-4-isopropyl-2,4,6-cycloheptatrien-1-one (158 mg, 0.42 mmol, 23%).

MS (m/z): 373 (M+H)$^+$; $^1$H-NMR (CDCl$_3$) δ (ppm): 1.29 (6 H, d, J=6.8 Hz), 2.69 (4 H, m), 2.91 (1 H, qui, J=6.9 Hz), 3.23 (4 H, m), 3.76 (2 H, s), 6.75–6.89 (3 H), 7.01 (1 H, dd, J=10.6, 1.7 Hz), 7.16 (1 H, t, J=8.1 Hz), 7.35 (1 H, d, J=1.7 Hz), 7.81 (1 H, d, J=10.6 Hz).

EXAMPLE 4

Production of 7-[4-(4-chlorophenyl)piperazino-1-methyl]-2-hydroxy-4-isopropyl-2,4,6-cycloheptatrien-1-one The same process using hinokitiol (300 mg, 1.83 mmol) and 1-(4-chlorophenyl)piperazine dihydrochloride (493 mg, 1.83 mmol) as carried out in Example 2 produced 7-[4-(4-chlorophenyl)piperazino-1-methyl]-2-hydroxy-4-isopropyl-2,4,6-cycloheptatrien-1-one (50 mg, 0.13 mmol, 7%).

MS (m/z): 373 (M+H)$^+$; $^1$H-NMR (CDCl$_3$) δ (ppm): 1.28 (6 H, d, J=6.8 Hz), 2.65–2.73 (4 H, m), 2.91 (1 H, qui, J=6.8 Hz), 3.13–3.22 (4 H, m), 3.76 (2 H, m), 6.80–6.89 (3 H), 7.00 (1 H, dd, J=0.6, 1.6 Hz), 7.20 (1 H, m), 7.34 (1 H, d, J=1.6 Hz), 7.81 (1 H, d, J=10.6 Hz).

EXAMPLE 5

Production of 2-hydroxy-4-isopropyl-7-[4-(2-methoxyphenyl)piperazino-1-methyl]-2,4,6-cycloheptatrien-1-one The same process using hinokitiol (200 mg, 1.22 mmol) and 1-(2-methoxyphenyl)piperazine (235 mg, 1.22 mmol) as carried out in Example 1 produced 2-hydroxy-4-isopropyl-7-[4-(2-methoxyphenyl)piperazino-1-methyl]-2,4,6-cycloheptatrien-1-one (95 mg, 0.26 mmol, 21%).

MS (m/z): 369 (M+H)$^+$; $^1$H-NMR (CDCl$_3$) δ (ppm): 1.28 (6 H, d, J=6.8 Hz), 2.76 (4 H, t, J=4.8 Hz), 2.91 (1 H, qui, J=6.8 Hz), 3.13 (4 H, t, J=4.8 Hz), 3.80 (2 H, s), 3.86 (3 H, s), 6.83–7.06 (5 H), 7.34 (1 H, d, J=1.6 Hz), 7.81 (1 H, d, J=10.6 Hz).

EXAMPLE 6

Production of 2-hydroxy-4-isopropyl-7-[4-(4-methoxyphenyl)piperazino-1-methyl]-2,4,6-cycloheptatrien-1-one The same process using hinokitiol (300 mg, 1.83 mmol) and 1-(4-methoxyphenylphenyl)piperazine hydrochloride (418 mg, 1.83 mmol) as carried out in Example 2 produced 2-hydroxy-4-isopropyl-7-[4-(4-methoxy-2-methylphenyl)piperazino-1-methyl]-2,4,6-cycloheptatrien-1-one (219 mg, 0.59 mmol, 32%).

MS (m/z): 369 (M+H)$^+$; $^1$H-NMR (CDCl$_3$) δ (ppm): 1.28 (6 H, d, J=6.8 Hz), 2.72 (4 H, m), 2.91 (1 H, qui, J=6.8 Hz), 3.13 (4 H, m), 3.77 (5 H, s), 6.80–7.04 (5 H), 7.34 (1 H, d, J=1.7 Hz), 7.81 (1 H, d, J=10.6 Hz).

EXAMPLE 7

Production of 7-[4-(4-fluorophenyl)piperazino-1-methyl]-2-hydroxy-4-isopropyl-2,4,6-cycloheptatrien-1-one The same process using hinokitiol (300 mg, 1.83 mmol) and 1-(4-fluorophenyl)piperazine (329 mg, 1.83 mmol) as carried out in Example 1 produced 7-[4-(4-fluorophenyl)piperazino-1-methyl]-2-hydroxy-4-isopropyl-2,4,6-cycloheptatrien-1-one (180 mg, 0.50 mmol, 28%).

MS (m/z): 357 (M+H)⁺; ¹H-NMR (CDCl₃) δ (ppm): 1.29 (6 H, d, J=6.8 Hz), 2.71 (4 H, m), 2.91 (1 H, qui, J=6.9 Hz), 3.16 (4 H, m), 3.77 (2 H, m), 6.84–7.04 (5 H), 7.79 (1 H, d, J=1.7 Hz), 7.81 (1 H, d, J=10.6 Hz).

EXAMPLE 8

Production of 2-hydroxy-4-isopropyl-7-[4-(3-methylphenyl)piperazino-1-methyl]-2,4,6-cycloheptatrien-1-one The same process using hinokitiol (300 mg, 1.83 mmol) and 1-(3-methylphenyl)piperazine dihydrochloride (456 mg, 1.83 mmol) as carried out in Example 2 produced 2-hydroxy-4-isopropyl-7-[4-(3-methylphenyl)piperazino-1-methyl]-2,4,6-cycloheptatrien-1-one (60 mg, 0.17 mmol, 9%).

¹H-NMR (CDCl₃) δ (ppm): 1.29 (6 H, d, J=6.8 Hz), 2.32 (3 H, s), 2.71 (4 H, m), 2.91 (1 H, qui, J=6.9 Hz), 3.23 (4 H, m), 3.76 (2 H, s), 6.67–6.77 (3 H), 7.01 (1 H, dd, J=10.6, 1.7 Hz), 7.16 (1 H, td, J=7.1, 1.7 Hz), 7.34 (1 H, d, J=1.7 Hz), 7.83 (1 H, d, J=10.6 Hz).

EXAMPLE 9

Production of 2-hydroxy-4-isopropyl-7-[4-(4-methylphenyl)piperazino-1-methyl]-2,4,6-cycloheptatrien-1-one The same process using hinokitiol (300 mg, 1.83 mmol) and 1-(4-methylphenyl)piperazine dihydrochloride (456 mg, 1.83 mmol) as carried out in Example 2 produced 2-hydroxy-4-isopropyl-7-[4-(4-methylphenyl)piperazino-1-methyl]-2,4,6-cycloheptatrien-1-one (97 mg, 0.27 mmol, 15%).

MS (m/z): 353 (M+H)⁺; ¹H-NMR (CDCl₃) δ (ppm): 1.28 (6 H, d, J=7.0 Hz), 2.27 (3 H, s), 2.71 (4 H, m), 2.91 (1 H, qui, J=7.0 Hz), 3.19 (4 H, m), 3.77 (2 H, s), 6.82–6.89 (2 H), 7.00 (1 H, dd, J=10.6, 1.7 Hz), 7.08 (2 H, m), 7.34 (1 H, d, J=1.7 Hz), 7.82 (1 H, d, J=10.6 Hz).

EXAMPLE 10

Production of 7-[4-(2-ethylphenyl)piperazino-1-methyl]-2-hydroxy-4-isopropyl-2,4,6-cycloheptatrien-1-one The same process using hinokitiol (300 mg, 1.83 mmol) and 1-(2-ethylphenyl)piperazine hydrochloride (415 mg, 1.83 mmol) as carried out in Example 2 produced 7-[4-(2-ethylphenyl)piperazino-1-methyl]-2-hydroxy-4-isopropyl-2,4,6-cycloheptatrien-1-one (76 mg, 0.21 mmol, 11%).

MS (m/z): 367 (M+H)⁺; ¹H-NMR (CDCl₃) δ (ppm): 1.24 (3 H, t, J=7.5 Hz), 1.29 (6 H, d, J=6.9 Hz), 2.65–2.77 (6 H), 2.91 (1 H, qui, J=6.9 Hz), 2.97 (4 H, t, J=4.6 Hz), 3.82 (2 H, s), 6.98–7.26 (5 H), 7.35 (1 H, d, J=1.7 Hz), 7.83 (1 H, d, J=10.6 Hz).

EXAMPLE 11

Production of 2-hydroxy-4-isopropyl-7-[4-(3-methylthio phenyl)piperazino-1-methyl]-2,4,6-cycloheptatrien-1-one The same process using hinokitiol (300 mg, 1.83 mmol) and 1-(3-methylthiophenyl)piperazine hydrochloride (448 mg, 1.83 mmol) as carried out in Example 2 produced 2-hydroxy-4-isopropyl-7-[4-(3-methylthiophenyl) piperazino-1-methyl]-2,4,6-cycloheptatrien-1-one (109 mg, 0.28 mmol, 15%).

MS (m/z): 385 (M+H)⁺; ¹H-NMR (CDCl₃) δ (ppm): 1.28 (6 H, d, J=6.8 Hz), 2.41 (3 H, s), 2.75 (4 H, t, J=4.7 Hz), 2.91 (1 H, qui, J=6.8 Hz), 3.07 (4 H, t, J=4.7 Hz), 3.80 (2 H, s), 7.00 (1 H, dd, J=10.8, 1.7 Hz), 7.05–7.13 (4 H), 7.34 (1 H, d, J=1.7 Hz), 7.80 (1 H, d, J=10.8 Hz).

EXAMPLE 12

Production of 7-[4-(2,5-dimethylphenyl)piperazino-1-methyl]-2-hydroxy-4-isopropyl-2,4,6-cycloheptatrien-1-one The same process using hinokitiol (300 mg, 1.83 mmol) and 1-(2,5-dimethylphenyl)piperazine (348 mg, 1.83 mmol) as carried out in Example 1 produced 7-[4-(2,5-dimethylphenyl)piperazino-1-methyl]-2-hydroxy-4-isopropyl-2,4,6-cycloheptatrien-1-one (348 mg, 0.95 mmol, 52%).

MS (m/z): 367 (M+H)⁺; ¹H-NMR (CDCl₃) δ (ppm): 1.09 (6 H, d, J=6.4 Hz), 2.19 (3 H, s), 2.25 (3 H, s), 2.50–2.95 (9 H), 3.40–3.80 (2 H), 6.60–6.78 (3 H), 7.01 (1 H, d, J=8.0 Hz), 7.05–7.20 (1 H, br), 7.40–7.60 (1 H, br).

EXAMPLE 13

Production of 7-[4-(4-chloro-2-methylphenyl) piperazino-1-methyl]-2-hydroxy-4-isopropyl-2,4,6-cycloheptatrien-1-one The same process using hinokitiol (0.65 g, 3.9 mmol) and 1-(4-chloro-2-methylphenyl)piperazine (0.84 g, 4.0 mmol) as carried out in Example 1 produced 7-[4-(4-chloro-2-methylphenyl)piperazino-1-methyl]-2-hydroxy-4-isopropyl-2,4,6-cycloheptatrien-1-one (1.5 g, 3.3 mmol, 84%).

¹H-NMR (CD₃OD) δ (ppm): 1.31 (6 H, d, J=6.8 Hz), 2.32 (3 H, s), 2.81–3.70 (9 H), 4.52 (2 H, s), 7.05–7.23 (4 H), 7.46 (1 H, d, J=1.6 Hz), 7.85 (1 H, d, J=9.9 Hz).

EXAMPLE 14

Production of 2-hydroxy-4-isopropyl-7-[4-(4-nitrophenyl)piperazino-1-methyl]-2,4,6-cycloheptatrien-1-one The same process using hinokitiol (1.0 g, 6 mmol) and 1-(4-nitrophenyl)piperazine (1.2 g, 6 mmol) as carried out in Example 1 produced 2-hydroxy-4-isopropyl-7-[4-(4-nitrophenyl)piperazino-1-methyl]-2,4,6-cycloheptatrien-1-one (1.1 g, 3 mmol, 50%).

MS (m/z): 384 (M+H)⁺; ¹H-NMR (CD₃OD) δ (ppm): 1.31 (6 H, d, J=7.0 Hz), 3.01 (1 H, qui, J=6.9 Hz), 3.30–3.70 (8 H), 4.52 (2 H, s), 7.06–7.19 (3 H), 7.46 (1 H, d, J=1.6 Hz), 7.85 (1 H, d, J=9.9 Hz), 8.12–8.20 (2 H).

EXAMPLE 15

Production of 2-hydroxy-4-isopropyl-7-4-(2-pyridyl) piperazino-1-methyl]-2,4,6-cycloheptatrien-1-one The same process using hinokitiol (300 mg, 1.83 mmol) and 1-(2-pyridyl)piperazine (299 mg, 1.83 mmol) as carried out in Example 1 produced 2-hydroxy-4-isopropyl-7-[4-(2-pyridyl) piperazino-1-methyl]-2,4,6-cycloheptatrien-1-one (285 mg, 0.84 mmol, 46%).

MS (m/z): 340 (M+H)⁺; ¹H-NMR (CDCl₃) δ (ppm): 1.29 (6 H, d, J=7.0 Hz), 2.66 (4 H, t, J=5.1 Hz), 2.91 (1 H, qui, J=6.8 Hz), 3.59 (4 H, t, J=5.1 Hz), 3.76 (2 H, s), 6.59–6.67

(1 H, m), 7.01 (1 H, dd, J=10.6, 1.7 Hz), 7.35 (1 H, d, J=1.7 Hz), 7.48 (1 H, m), 7.84 (1 H, d, J=10.6 Hz), 8.19 (1 H, m).

EXAMPLE 16

Production of 2-hydroxy-4-isopropyl-7-(3-methyl-4-phenyl-piperazino-1-methyl)-2,4,6-cycloheptatrien-1-one The same process using hinokitiol (300 mg, 1.83 mmol) and 2-methyl-1-phenylpiperazine (323 mg, 1.83 mmol) as carried out in Example 1 produced 2-hydroxy-4-isopropyl-7-(3-methyl-4-phenylpiperazino-1-methyl)-2,4,6-cycloheptatrien-1-one (280 mg, 0.79 mmol, 43%).

$^1$H-NMR (CDCl$_3$) δ (ppm): 1.13 (3 H, d, J=6.4 Hz), 1.29 (6 H, d, J=6.9 Hz), 2.48–2.60 (1 H, m), 2.67 (2 H, d, J=3.6 Hz), 2.80–2.98 (2 H, m), 3.11–3.29 (2 H, m), 3.75 (2 H, s), 3.81–3.95 (1 H, m), 6.82–7.05 (4 H), 7.23–7.36 (3 H), 7.90 (1 H, d, J=10.6 Hz).

EXAMPLE 17

Production of 7-(4-benzylpiperidino-1-methyl)-2-hydroxy-4-isopropyl-2,4,6-cycloheptatrien-1-one To hinokitiol (500 mg, 3.0 mmol), 4-benzylpiperidine (640 mg, 3.6 mmol) and acetic acid (0.21 ml, 3.6 mmol) dissolved in methanol 3 ml was added 37% aqueous formalin solution (0.27 ml, 3.6 mmol) before heating at 60° C. for 2.5 hrs. The solution was diluted with water and mixed with ethyl acetate, 1N HCl, and methylene chloride in this order to extract. The extract solution was dried over magnesium sulfate and concentrated under reduced pressure to precipitate crystal, which was suspended in ether and separated by filtration to give 7-(4-benzylpiperidino-1-methyl)-2-hydroxy-4-isopropyl-2,4,6-cycloheptatrien-1-one (815 mg, 2.3 mmol, 76%).

$^1$H-NMR (CDCl$_3$) δ (ppm): 1.25 (6 H, d, J=6.9 Hz), 1.45~1.70 (3 H), 2.09 (2 H, td, J=9.7, 1.8 Hz), 2.55 (2 H, d, J=6.2 Hz), 2.80–2.96 (3 H), 3.65 (2 H, s), 6.97 (1 H, dd, J=10.7, 1.7 Hz), 7.10–7.33 (6 H), 7.75 (1 H, d, J=10.7 Hz).

EXAMPLE 18

Production of 7-(4-benzylpiperazino-1-methyl)-2-hydroxy-4-isopropyl-2,4,6-cycloheptatrien-1-one hydrochloride To hinokitiol (500 mg, 3.0 mmol), 1-benzylpiperazine (0.7 ml, 4 mmol) and acetic acid (0.24 ml, 4 mmol) dissolved in methanol 5 ml was added 37% aqueous formalin solution (0.5 ml, 6 mmol) before heating at 60° C. for 2.5 hrs. The solution was diluted with water and mixed with ethyl acetate, 1N HCl, and solvent mixture of methylene chloride:isopropanol (3:1) in this order to extract. The extract solution was dried over magnesium sulfate and concentrated under reduced pressure to precipitate crystal, which was suspended in ethyl acetate and separated by filtration to give 7-(4-benzylpiperazino-1-methyl)-2-hydroxy-4-isopropyl-2,4,6-cycloheptatrien-1-one hydrochloride (380 mg, 0.9 mmol, 35%).

MS (m/z): 353 (M+H)$^+$; $^1$H-NMR (CDCl$_3$) δ (ppm): 1.27 (6 H, d, J=6.8 Hz), 2.45–2.65 (8 H, br), 2.89 (1 H, qui, J=6.8 Hz), 3.54 (2 H, s), 3.70 (2 H, s), 6.97 (1 H, dd, J=10.7, 1.7 Hz), 7.20–7.35 (6 H), 7.75 (1 H, d, J=10.7 Hz).

EXAMPLE 19

Production of 2-ethoxy-4-isopropyl-7-(4-phenylpiperazino-1-methyl)-2,4,6-cycloheptatrien-1-one To 2-hydroxy-4-isopropyl-7-(4-phenylpiperazino-1-methyl)-2,4,6-cycloheptatrien-1-one (11.0 g, 32.5 mmol) and potassium carbonate (6.2 g, 45 mmol) suspended in acetone 150 ml was added diethyl sulfate (5.1 ml, 39 mmol) before heating under reflux for 6 hrs. The reaction solution was filtered to remove potassium carbonate and concentrated under reduced pressure to give a residue, which was mixed with ethyl acetate and washed with saturated NaCl solution. The resultant solution was dried over magnesium sulfate and concentrated under reduced pressure to give a residue, which was purified by silica gel chromatography (elution solvent:ethyl acetate) to obtain 2-ethoxy-4-isopropyl-7-(4-phenylpiperazino-1-methyl)-2,4,6-cycloheptatrien-1-one (6.3 g, 17.1 mmol, 53%).

$^1$H-NMR (CDCl$_3$) δ (ppm): 1.27 (6 H, d, J=6.9 Hz), 1.55 (3 H, t, J=6.9 Hz), 2.70 (4 H, t, J=5.1 Hz), 2.86 (1 H, qui, J=6.9 Hz), 3.23 (4 H, t, J=5.1 Hz), 3.70 (2 H, s), 4.14 (2 H, q, J=6.9 Hz), 6.73 (1 H, s), 6.81–6.95 (3 H), 7.22–7.32 (3 H), 7.72 (1 H, d, J=9.5 Hz).

EXAMPLE 20

Production of 7-[4-(4-chloro-2-methylphenyl)piperazino-1-methyl]-2-ethoxy-4-isopropyl-2,4,6-cycloheptatrien-1-one The same process using 2-hydroxy-4-isopropyl-7-[4-(4-chloro-2-methylphenyl)piperazino-1-methyl]-2,4,6-cycloheptatrien-1-one (1.40 g, 3.6 mmol) and diethyl sulfate (0.94 ml, 7.2 mmol) as carried out in Example 19 produced 7-[4-(4-chloro-2-methylphenyl)piperazino-1-methyl]-2-ethoxy-4-isopropyl-2,4,6-cycloheptatrien-1-one (0.61 g, 1.5 mmol, 41%).

$^1$H-NMR (CDCl$_3$) δ (ppm): 1.27 (6 H, d, J=6.9 Hz), 1.54 (3 H, t, J=6.9 Hz), 2.27 (3 H, s), 2.66–2.72 (4 H), 2.78–2.95 (5 H), 3.70 (2 H, s), 4.14 (2 H, q, J=6.9 Hz), 6.73 (1 H, d, J=1.1 Hz), 6.84 (1 H, dd, J=9.5, 1.1 Hz), 6.94 (1 H, d, J=8.4 Hz) 7.09–7.14 (2 H), 7.72 (1 H, d, J=9.5 Hz).

EXAMPLE 21

Production of 2-ethoxy-4-isopropyl-7-[4-(4-nitrophenyl)piperazino-1-methyl]-2,4,6-cycloheptatrien-1-one The same process using 2-hydroxy-4-isopropyl-7-[4-(4-nitrophenyl)piperazino-1-methyl]-2,4,6-cycloheptatrien-1-one (1.0 g, 2.7 mmol) and diethyl sulfate (0.46 ml, 3.5 mmol) as carried out in Example 19 produced 2-ethoxy-4-isopropyl-7-[4-(4-nitrophenyl)piperazino-1-methyl]-2,4,6-cycloheptatrien-1-one (0.41 g, 0.8 mmol, 31%).

MS (m/z): 412 (M+H)$^+$; $^1$H-NMR (CDCl$_3$) δ (ppm): 1.28 (6 H, d, J=6.9 Hz), 1.55 (3 H, t, J=7.0 Hz), 2.66–2.71 (4 H), 2.86 (1 H, qui, J=6.9 Hz), 3.42–3.48 (4 H), 3.70 (2 H, s), 4.14 (2 H, q, J=7.0 Hz), 6.73 (1 H, d, J=1.4 Hz), 6.78–6.86 (3 H), 7.68 (1 H, d, J=9.4 Hz), 8.08–8.16 (2 H).

EXAMPLE 22

Production of 2-butoxy-4-isopropyl-7-(4-phenylpiperazino-1-methyl)-2,4,6-cycloheptatrien-1-one The same process using 2-hydroxy-4-isopropyl-7-(4-phenylpiperazino-1-methyl)-2,4,6-cycloheptatrien-1-one (430 mg, 1.3 mmol) and n-butyl iodide (0.17 ml, 1.5 mmol) as carried out in Example 19 produced 2-butoxy-4-isopropyl-7-(4-phenylpiperazino-1-methyl)-2,4,6-cycloheptatrien-1-one (207 mg, 0.5 mmol, 41%).

MS (m/z): 395 (M+H)$^+$; $^1$H-NMR (CDCl$_3$) δ (ppm): 0.99 (3 H, t, J=7.3 Hz), 1.27 (6 H, d, J=6.9 Hz), 1.56 (2 H, m), 1.93 (2 H, m), 2.70 (4 H, t, J=5.0 Hz), 2.85 (1 H, qui, J=7.0 Hz), 3.23 (4 H, t, J=5.0 Hz), 3.69 (2 H, s), 4.05 (2 H, t, J=6.6 Hz), 6.73 (1 H, s), 6.81–6.97 (4 H), 7.20–7.32 (2 H), 7.71 (1 H, d, J=9.5 Hz).

EXAMPLE 23

Production of 2-benzyloxy-4-isopropyl-7-(4-phenylpiperazino-1-methyl)-2,4,6-cycloheptatrien-1-one The same process using 2-hydroxy-4-isopropyl-7-(4-phenylpiperazino-1-methyl)-2,4,6-cycloheptatrien-1-one (400 mg, 1.2 mmol) and benzyl bromide (0.18 ml, 1.5 mmol) as carried out in Example 19 produced 2-benzyloxy-4-isopropyl-7-(4-phenylpiperazino-1-methyl)-2,4,6-cycloheptatrien-1-one (110 mg, 0.3 mmol, 22%).
With respect to the hydrochloride:

MS (m/z): 429 (M+H)$^+$; $^1$H-NMR (CD$_3$OD) δ (ppm): 1.20 (6 H, d, J=6.8 Hz), 2.96 (1 H, qui, J=6.9 Hz), 3.05–3.20 (2 H, m), 3.30–3.45 (2 H, m), 3.61 (2 H, m), 3.78 (2 H, m), 4.42 (2 H, s), 5.41 (2 H, s), 6.80–7.09 (4 H), 7.17 (1 H, d, J=1.1 Hz), 7.23–7.54 (7 H), 7.81 (1 H, d, J=9.5 Hz).

EXAMPLE 24

Production of 7-(4-benzylpiperazino-1-methyl)-2-ethoxy-4-isopropyl-2,4,6-cycloheptatrien-1-one To 7-(4-benzylpiperazino-1-methyl)-2-hydroxy-4-isopropyl-2,4,6-cycloheptatrien-1-one hydrochloride (300 mg, 0.7 mmol) and potassium carbonate (691 mg, 5 mmol) suspended in solvent mixture (8 ml) of acetone:water (15:1) was added diethyl sulfate (0.26 ml, 2 mmol) before heating under reflux for 4 hrs. The reaction solution was filtered to remove potassium carbonate and concentrated under reduced pressure to give a residue, which was mixed with ethyl acetate and washed with saturated NaCl solution. The resultant solution was dried over magnesium sulfate and concentrated under reduced pressure to give a residue, which was purified by silica gel chromatography (elution solvent: ethyl acetate) to obtain 7-(4-benzylpiperazino-1-methyl)-2-ethoxy-4-isopropyl-2,4,6-cycloheptatrien-1-one (122 mg, 0.3 mmol, 45%).

MS (m/z): 381 (M+H)$^+$; $^1$H-NMR (CDCl$_3$) δ (ppm): 1.26 (6 H, d, J=7.0 Hz), 1.53 (3 H, t, J=6.9 Hz), 2.40–2.70 (8 H, br), 2.84 (1 H, qui, J=6.8 Hz), 3.53 (2 H, s), 3.63 (2 H, s), 4.12 (2 H, q, J=6.9 Hz), 6.70 (1 H, s), 6.81 (1 H, d, J=9.5 Hz), 7.20–7.40 (5 H), 7.66 (1 H, d, J=9.5 Hz).

EXAMPLE 25

Production of 4-isopropyl-2-morpholino-7-(4-phenyl piperazino-1-methyl)-2,4,6-cycloheptatrien-1-one 2-ethoxy-4-isopropyl-7-(4-phenylpiperazino-1-methyl)-2,4,6-cycloheptatrien-1-one (500 mg, 1.4 mmol) and morpholine (0.18 ml, 2.1 mmol) were dissolved in toluene 6 ml before heating at 100° C. for 2 hrs. The solution was concentrated under reduced pressure to give a residue, which was purified by silica gel chromatography[elution solvent: methylene chloride-methanol (50:1)] to obtain 4-isopropyl-2-morpholino-7-(4-phenyl piperazino-1-methyl)-2,4,6-cycloheptatrien-1-one (150 mg, 0.37 mmol, 27%).

MS (m/z): 408 (M+H)$^+$; $^1$H-NMR (CDCl$_3$) δ (ppm): 1.25 (6 H, d, J=6.9 Hz), 2.65–2.70 (4 H, m), 2.82 (1 H, qui, J=6.9 Hz), 3.19–3.26 (8 H, m), 3.65 (2 H, s), 3.88–3.93 (4 H, m), 6.63–6.66 (1 H, br), 6.72 (1 H, d, J=9.5 Hz), 6.81–6.96 (3 H, m), 7.21–7.32 (2 H, m), 7.57 (1 H, d, J=9.5 Hz).

EXAMPLE 26

Production of 4-isopropyl-7-(4-phenylpiperazino-1-methyl)-2-piperidino-2,4,6-cycloheptatrien-1-one The same process using 2-ethoxy-4-isopropyl-7-(4-phenylpiperazino-1-methyl)-2,4,6-cycloheptatrien-1-one (500 mg, 1.4 mmol) and piperidine (0.2 ml, 2.0 mmol) as carried out in Example 25 produced 4-isopropyl-7-(4-phenylpiperazino-1-methyl)-2-piperidino-2,4,6-cycloheptatrien-1-one (548 mg, 1.4 mmol, 99%).

MS (m/z): 406 (M+H)$^+$; $^1$H-NMR (CDCl$_3$) δ (ppm): 1.25 (6 H, d, J=6.8 Hz), 1.50–1.84 (6 H, m), 2.65–2.70 (4 H, m), 2.80 (1 H, qui, J=6.8 Hz), 3.19–3.23 (8 H, m), 3.68 (2 H, s), 6.61–6.67 (2 H, m), 6.80–6.96 (3 H, m), 7.21–7.30 (2 H, m), 7.50 (1 H, d, J=9.2 Hz).

EXAMPLE 27

Production of 2-[(2-hydroxyethyl)amino]-4-isopropyl-7-(4-phenylpiperazino-1-methyl)-2,4,6-cycloheptatrien-1-one The same process using 2-ethoxy-4-isopropyl-7-(4-phenylpiperazino-1-methyl)-2,4,6-cycloheptatrien-1-one (168 mg, 0.46 mmol) and ethanolamine (1.0 ml, 1.7 mmol) as carried out in Example 25 produced 2-[(2-hydroxyethyl)amino]-4-isopropyl-7-(4-phenylpiperazino-1-methyl)-2,4,6-cycloheptatrien-1-one (124 mg, 0.33 mmol, 71%).

MS (m/z): 382 (M+H)$^+$; $^1$H-NMR (CDCl$_3$) δ (ppm): 1.29 (6 H, d, J=6.9 Hz), 2.68–2.73 (4 H, m), 2.89 (1 H, qui, J=6.9 Hz), 3.21–3.25 (4 H, m), 3.50–3.61 (2 H, m), 3.76 (2 H, s), 3.97 (2 H, t, J=5.3 Hz), 6.60 (1 H, s), 6.71 (1 H, d, J=10.3 Hz), 6.81–6.95 (3 H, m), 7.26 (2 H, t, J=7.6 Hz), 7.59–7.65 (1 H, m), 7.72 (1 H, d, J=10.3 Hz).

EXAMPLE 28

Production of 4-isopropyl-2-methylamino-7-(4-phenyl piperazino-1-methyl)-2,4,6-cycloheptatrion-1-one 2-ethoxy-4-isopropyl-7-(4-phenylpiperazino-1-methyl)-2,4,6-cycloheptatrien-1-one (500 mg, 1.4 mmol) and methylamine (1.0 ml (40% methanol solution), 10 mmol) were dissolved in toluene 6 ml before heating at 100° C. for 30 min. The solution was concentrated under reduced pressure to give a crude crystal, which was suspended in ether, and separated by filtration to obtain 4-isopropyl-2-methylamino-7-(4-phenylpiperazino-1-methyl)-2,4,6-cycloheptatrien-1-one (183 mg, 0.52 mmol, 38%).

MS (m/z): 352 (M+H)$^+$; $^1$H-NMR (CDCl$_3$) δ (ppm): 1.31 (6 H, d, J=6.8 Hz), 2.69–2.74 (4 H, m), 2.91 (1 H, qui, J=6.9 Hz), 3.06 (3 H, d, J=5.5 Hz), 3.21–3.26 (4 H, m), 3.77 (2 H, s), 6.48 (1 H, s), 6.69 (1 H, d, J=10.2 Hz), 6.80–6.95 (3 H, m), 7.22–7.30 (2 H, m), 7.43 (1 H, m), 7.72 (1 H, d, J=10.2 Hz).

EXAMPLE 29

Production of 4-isopropyl-2-(4-methylpiperazino)-7-(4-phenylpiperazino-1-methyl)-2,4,6-cycloheptatrien-1-one The same process using 2-ethoxy-4-isopropyl-7-(4-phenylpiperazino-1-methyl)-2,4,6-cycloheptatrien-1-one (400 mg, 1.1 mmol) and N-methylpiperazine (0.15 ml, 1.4 mmol) as carried out in Example 28 produced 4-isopropyl-2-(4-methylpiperazino)-7-(4-phenylpiperazino-1-methyl)-2,4,6-cycloheptatrien-1-one (348 mg, 0.83 mmol, 76%).

MS (m/z): 421 (M+H)+; 1H-NMR (CDCl$_3$) δ (ppm): 1.25 (6 H, d, J=6.9 Hz), 2.36 (3 H, s), 2.61–2.70 (8 H, m), 2.81 (1 H, qui, J=6.8 Hz), 3.19–3.30 (8 H, m), 3.66 (2 H, s), 6.67 (1 H, s), 6.69 (1 H, d, J=9.2 Hz), 6.89–6.95 (3 H, m), 7.15–7.30 (2 H, m), 7.55 (1 H, d, J=9.2 Hz).

EXAMPLE 30

Production of 2-[ (2-hydroxyethyl)methylamino]-4-isopropyl-7-(4-phenylpiperazino-1-methyl)-2,4,6-cycloheptatrien-1-one The same process using 2-ethoxy-4-isopropyl-7-(4-phenylpiperazino-1-methyl)-2,4,6-cycloheptatrien-1-one (254 mg, 0.69 mmol) and N-methylethanolamine (225 mg, 3.0 mmol) as carried out in Example 25 produced 2-[(2-hydroxyethyl)methylamino]-4-isopropyl-7-(4-phenylpiperazino-1-methyl)-2,4,6-cycloheptatrien-1-one (116 mg, 0.29 mmol, 42%).

1H-NMR (CDCl$_3$) δ (ppm): 1.26 (6 H, d, J=6.9 Hz), 2.66–2.71 (4 H, m), 2.82 (1 H, qui, J=6.9 Hz), 3.01 (3 H, s), 3.18–3.23 (4 H, m), 3.53 (2 H, t, J=5.2 Hz), 3.68 (2 H, s), 3.86 (2 H, t, J=5.2 Hz), 6.56–6.61 (2 H, m), 6.80–6.95 (3 H, m), 7.21–7.31 (2 H, m), 7.47 (1 H, d, J=9.5 Hz).

EXAMPLE 31

Production of 2-[(2-hydroxypropyl)amino]-4-isopropyl-7-(4-phenylpiperazino-1-methyl)-2,4,6-cycloheptatrien-1-one The same process using 2-ethoxy-4-isopropyl-7-(4-phenylpiperazino-1-methyl)-2,4,6-cycloheptatrien-1-one (248 mg, 0.68 mmol) and 2-hydroxypropylamine (239 mg, 3.2 mmol) as carried out in Example 25 produced 2-[(2-hydroxypropyl) amino]-4-isopropyl-7-(4-phenylpiperazino-1-methyl)-2,4,6-cycloheptatrien-1-one (202 mg, 0.51 mmol, 75%).

MS (m/z): 396 CM+H)+; 1H-NMR (CDCl$_3$) δ (ppm): 1.29 (6 H, d, J=6.9 Hz), 1.32 (3 H, d, J=7.5 Hz), 2.68–2.73 (4 H, m), 2.89 (1 H, qui, J=6.9 Hz), 3.20–3.25 (4 H, m), 3.67–3.98 (5 H, m), 6.68–6.72 (2 H, m), 6.80–6.95 (3 H, m), 7.21–7.31 (2 H, m), 7.42 (1 H, d, J=7.8 Hz) 7.70 (1 H, d, J=10.6 Hz).

EXAMPLE 32

Production of 2-[(2-hydroxyethoxy)ethylamino]-4-isopropyl-7-(4-phenylpiperazino-1-methyl)-2,4,6-cycloheptatrien-1-one The same process using 2-ethoxy-4-isopropyl-7-(4-phenylpiperazino-1-methyl)-2,4,6-cycloheptatrien-1-one (246 mg, 0.68 mmol) and 2-(2-hydroxyethoxy)ethylamine (239 mg, 2.3 mmol) as carried out in Example 25 produced 2-[(2-hydroxyethoxy)ethylamino]-4-isopropyl-7-(4-phenylpiperazino-1-methyl)-2,4,6-cycloheptatrien-1-one (246 mg, 0.58 mmol, 86%).

MS (m/z): 426 (M+H)+; 1H-NMR (CDCl$_3$) δ (ppm): 1.29 (6 H, d, J=6.9 Hz), 2.68–2.73 (4 H, m), 2.89 (1 H, qui, J=6.9 Hz), 3.21–3.26 (4 H, m), 3.49–3.67 (4 H, m), 3.74–3.80 (4 H, m), 3.83 (2 H, t, J=5.4 Hz), 6.55 (1 H, d, J=1.4 Hz), 6.70 (1 H, dd, J=10.2, 1.4 Hz), 6.80–6.96 (3 H, m), 7.20–7.30 (2 H, m), 7.60 (1 H, t, J=5.2 Hz), 7.71 (1 H, d, J=10.2 Hz).

EXAMPLE 33

Production of 2-butylamino-4-isopropyl-7-(4-phenyl piperazino-1-methyl)-2,4,6-cycloheptatrien-1-one The same process using 2-ethoxy-4-isopropyl-7-(4-phenylpiperazino-1-methyl)-2,4,6-cycloheptatrien-1-one (266 mg, 0.73 mmol) and n-butylamine (2 ml, 20 mmol) as carried out in Example 25 produced 2-butylamino-4-isopropyl-7-(4-phenylpiperazino-1-methyl)-2,4,6-cycloheptatrien-1-one (236 mg, 0.60 mmol, 82%).

MS (m/z): 394 (M+H)+; 1H-N MR (CDC$_3$) δ (ppm): 0.99 (3 H, t, J=7.2 Hz), 1.30 (6 H, d, J=6.9 Hz), 1.41–1.59 (2 H, m), 1.68–1.83 (2 H, m), 2.68–2.73 (4 H, m), 2.89 (1 H, qui, J=6.9 Hz), 3.21–3.26 (4 H, m), 3.30–3.36 (2 H, m), 3.76 (2 H, s), 6.50 (1 H, d, J=1.4 Hz), 6.67 (1 H, dd, J=10.2, 1.4 Hz), 6.79–6.95 (3 H, m), 7.20–7.29 (2 H, m), 7.39–7.43 (1 H, m), 7.69 (1 H, d, J=0.2 Hz).

EXAMPLE 34

Production of 2-benzylamino-4-isopropyl-7-(4-phenylpiperazino-1-methyl)-2,4,6-cycloheptatrien-1-one The same process using 2-ethoxy-4-isopropyl-7-(4-phenylpiperazino-1-methyl)-2,4,6-cycloheptatrien-1-one (259 mg, 0.71 mmol) and benzylamine (200 mg, 1.9 mmol) as carried out in Example 25 produced 2-benzylamino-4-isopropyl-7-(4-phenylpiperazino-1-methyl)-2,4,6-cycloheptatrien-1-one (153 mg, 0.36 mmol, 51%).

MS (m/z): 428 CM+H)+; 1H-NMR (CDCl$_3$) δ (ppm): 1.14 (6 H, d, J=6.8 Hz), 2.69–2.74 (4 H, m), 2.78 (1 H, qui, J=6.8 Hz), 3.21–3.26 (4 H, m), 3.78 (2 H, s), 4.57 (2 H, d, J=5.8 Hz), 6.49 (1 H, d, J=1.3 Hz), 6.67 (1 H, dd, J=10.2, 1.3 Hz), 6.80–6.96 (3 H, m), 7.22–7.36 (7 H, m), 7.71 (1 H, d, J=10.2 Hz), 7.72–7.78 (1 H, m)

EXAMPLE 35

Production of 2-dimethylamino-4-isopropyl-7-(4-phenylpiperazino-1-methyl)-2,4,6-cycloheptatrien-1-one 2-ethoxy-4-isopropyl-7-(4-phenylpiperazino-1-methyl)-2,4,6-cycloheptatrien-1-one (393 mg, 1.1 mmol) dissolved in toluene 3 ml was cooled to −30° C. and bubbled with dimethylamine gas before stirring at ambient temperature for 5 hrs. The reaction solution was concentrated under reduced pressure to give a residue, which was purified by silica gel chromatography[elution solvent: hexane-ethyl acetate (1:1)] to obtain 2-dimethylamino-4-isopropyl-7-(4-phenylpiperazino-1-methyl)-2,4,6-cycloheptatrien-1-one (165 mg, 0.45 mmol, 42%).

MS (m/z): 366 (M+H)+; 1H-NMR (CDCl$_3$) δ (ppm): 1.24 (6 H, d, J=6.8 Hz), 2.65–2.70 (4 H, m), 2.79 (1 H, qui, J=6.8 Hz), 3.03 (6 H, s), 3.17–3.22 (4 H, m), 3.68 (2 H, s), 6.42 (1 H, d, J=1.2 Hz), 6.51 (1 H, dd, J=9.4, 1.2 Hz), 6.80–6.96 (3 H, m), 7.20–7.30 (2 H, m), 7.42 (1 H, d, J=9.4 Hz).

EXAMPLE 36

Production of 7-[4-(4-chloro-2-methylphenyl) piperazino-1-methyl]-2-[(2-hydroxyethyl)amino]-4-isopropyl-2,4,6-cycloheptatrien-1-one The same process using 7-[4-(4-chloro-2-methylphenyl) piperazino-1-methyl]-2-ethoxy-4-isopropyl-2,4,6-cycloheptatrien-1-one (433 mg, 1.0 mmol) and ethanolamine (96 mg, 1.6 mmol) as carried out in Example 25 produced 7-[4-(4-chloro-2-methylphenyl)piperazino-1-methyl]-2-[(2-hydroxy ethyl)amino]-4-isopropyl-2,4,6-cycloheptatrien-1-one (203 mg, 0.47 mmol, 45%).

1H-NMR (CDCl$_3$) δ (ppm): 1.29 (6 H, d, J=6.9 Hz), 2.27 (3 H, s), 2.65–2.73 (4 H1), 2.82–2.96 (5 H), 3.54 (2 H, q, J=5.5 Hz), 3.76 (2 H, s), 3.97 (2 H, t, J=5.4 Hz), 6.60 (1 H, d, J=1.2 Hz), 6.71 (1 H, dd, J=10.2, 1.2 Hz), 6.94 (1 H, d, J=8.1 Hz), 7.08 (1 H, d, J=2.3 Hz), 7.13 (1 H, s), 7.57–7.64 (1 H, br), 7.72 (1 H, d, J=10.2 Hz).

EXAMPLE 37

Production of 2-ethoxy-7-[4-(4-fluorophenyl) piperazino-1-methyl]-4-isopropyl-2,4,6-cycloheptatrien-1-one The same process using 7-[4-(4-fluorophenyl)piperazino-1-methyl]-2-hydoxy-4-isopropyl-2,4,6-cycloheptatrien-1-one (6.0 g, 16.8 mmol) and diethyl sulfate (2.6 ml, 20.0 mmol) as carried out in Example 19 produced 2-ethoxy-7-[4-(4-fluorophenyl)piperazino-1-methyl]-4-isopropyl-2,4,6-cycloheptatrien-1-one (3.7 g, 9.6 mmol, 57%).

MS (m/z): 385 (M+H)$^+$; $^1$H-NMR (CDCl$_3$) δ (ppm): 1.27 (6 H, d, J=6.9 Hz), 1.54 (3 H, t, J=7.0 Hz), 2.65–2.75 (4 H), 2.90 (1 H, qui, J=6.9 Hz), 3.10–3.20 (4 H), 3.70 (2 H, s), 4.07–4.20 (2 H), 6.73 (1 H, br), 6.80–7.02 (5 H), 7.70 (1 H, d, J=9.4 Hz).

EXAMPLE 38

Production of 2-benzyloxy-7-[4-( 4-fluorophenyl) piperazino-1-methyl]-4-isopropyl-2,4,6-cycloheptatrien-1-one To 7-[4-(4-fluorophenyl)piperazino-1-methyl]-2-hydoxy-4-isopropyl-2,4,6-cycloheptatrien-1-one (1.5 g, 4.2 mmol) dissolved in dimethylformamide 10 ml was added sodium hydride (0.25 g, 6.3 mmol) little by little under ice-cooling before stirring for 30 min. To the solution was added benzyl bromide (2.6 ml, 20.0 mmol) dropwise under ice-cooling before stirring for 2 hrs. The reaction solution was poured into ice-water and mixed with ethyl acetate to extract. The extract solution was washed with saturated NaCl solution, dried over magnesium sulfate, and concentrated under reduced pressure to give a residue, which was purified by silica gel chromatography[elution solvent: hexane-ethyl acetate (1:1)] to obtain 2-benzyloxy-7-[4-(4-fluorophenyl) piperazino-1-methyl]-4-isopropyl-2,4,6-cycloheptatrien-1-one (0.35 g, 0.77 mmol, 18%).
With respect to the hydrochloride:

$^1$H-NMR (CD$_3$OD) δ (ppm): 1.20 (6 H, d, J=6.9 Hz), 2.89–3.03 (1 H, m), 3.06–3.80 (8 H), 4.43 (2 H, s), 5.41 (2 H, s), 7.00–7.09 (5 H), 7.17 (1 H, s), 7.33–7.54 (5 H), 7.82 (1 H, d, J=9.4 Hz).

EXAMPLE 39

Production of 7-(4-(4-fluorophenyl)piperazino- 1-methyl]-2-[2-(hydroxyethyl)amino]-4-isopropyl-2,4, 6-cycloheptatrien-1-one The same process using 2-ethoxy-7-[4-(4-fluorophenyl) piperazino-1-methyl]-4-isopropyl-2,4,6-cycloheptatrien-1-one (2.0 g, 5.2 mmol) and ethanolamine (1 ml, 16.4 mmol) as carried out in Example 25 produced 7-[4-(4-fluorophenyl) piperazino-1-methyl]-2-[2-(hydroxyethyl)amino]-4-isopropyl-2,4,6-cycloheptatrien-1-one (1.6 g, 4.0 mmol, 77%).

MS (m/z): 400 [M+H]$^+$; $^1$H-NMR (CDCl$_3$) δ (ppm): 1.29 (6 H, d, J=6.9 Hz), 2.65–2.75 (4 H), 2.89 (1 H, qui, J=6.9 Hz), 3.11–3.18 (4 H), 3.49–3.59 (2 H, m), 3.76 (2 H, s), 3.93–4.00 (2 H, m), 6.60 (1 H, br), 6.67–6.74 (1 H, m), 6.83–7.01 (4 H), 7.58–7.66 (1 H, br), 7.71 (1 H, d, J=10.0 Hz).

Industrial Availability

A compound having tropone structure according to the present invention has excellent effects, e.g. (1) to increase a bladder capacity and prolongate an urination intervals because of inhibitory action on urination reflexes, (2) to avoid bringing about dry mouth and ischuria, the side effects of ananticholinergic agent, and (3) to act on patients even with increasing atoropine-resistant contraction detected. It is expected to be a novel remedy for pollakiurea and urinary incontinence, because it is equal to or higher than the current corresponding ones in efficiency.

What is claimed is:

1. A compound represented by the formula (3):

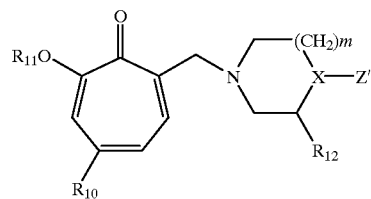

(3)

where $R_{10}$ represents a hydrogen atom or a $C_1$ to $C_5$ alkyl group, $R_{11}$ represents a hydrogen atom, a $C_1$ to $C_5$ alkyl group, or an unsubstituted benzyl group, or a $C_1$ to $C_5$ acyl group, $R_{12}$ represents a hydrogen atom or a $C_1$ to $C_3$ alkyl group, Z' represents an unsubstituted or substituted phenyl, an unsubstituted benzyl or an unsubstituted 2-pyridyl group, wherein the substituent group on the phenyl group is a substituent group selected from a $C_1$ to $C_5$ alkyl group, halogen, nitro group, cyano group and a lower alkoxy group, X represents a nitrogen atom, and m is an integer of 1, or pharmaceutically acceptable salts thereof.

2. The compound according to claim 1, wherein $R_{10}$ represents an isopropyl group, $R_{11}$ represents a hydrogen atom, a $C_1$ to $C_5$ alkyl group or a benzyl group, $R_{12}$ represents a hydrogen atom and Z' represents an unsubstituted phenyl group, or a phenyl group substituted with 1 to 2 groups selected from lower alkyl groups or halogens, or pharmaceutically acceptable salts thereof.

3. The compound according to claim 2, wherein $R_{11}$ is an ethyl group or a benzyl group, Z' is an unsubstituted phenyl group or a 4-fluorophenyl group, or pharmaceutically acceptable salts thereof.

4. A pharmaceutical composition comprising the compound according to any one of claims 1, 2 or 3 or a pharmaceutically acceptable salt thereof as an active ingredient, and a pharmaceutically acceptable carrier.

5. A compound represented by the formula (4):

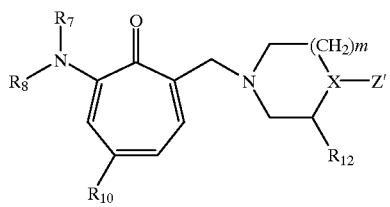

(4)

wherein $R_{10}$ represents a hydrogen atom or a $C_1$ to $C_5$ alkyl group, $R_7$ and $R_8$ are the same or different and represent a hydrogen atom, an optionally substituted lower alkyl group or an unsubstituted aralkyl group, or $R_7$ and $R_8$ are combined to form a 5- to 7-membered ring which may contain 1 to 3 —O— or —NR$_9$— residues, R$_{12}$ represents a hydrogen atom, R$_9$ represents a hydrogen atom or a lower alkyl group, Z' represents an unsubstituted or substituted phenyl, group, wherein the substituent group on phenyl group is a substituent group selected from a C$_1$ to C$_5$ alkyl group and halogen, X represents a nitrogen atom and m is an integer of 1 or pharmaceutically acceptable salts thereof.

6. The compound according to claim 5, wherein a substituent group on a lower alkyl group in R$_7$ and R$_8$ is a substituent group selected from a hydroxyl group and a C$_1$ to C$_5$ alkoxy group whereupon the number of carbon atoms in the alkyl group is 1 to 5; and a substituent group on a phenyl group in Z' is a substituent group selected from a C$_1$ to C$_5$ alkyl group and halogen, or pharmaceutically acceptable salts thereof.

7. The compound according to claim 5 or 6, wherein R$_{10}$ represents a C$_1$ to C$_5$ alkyl group, NR$_7$R$_8$ represents a C$_2$ to C$_5$ alkylamino group having a hydroxyl group, Z' represents an unsubstituted or substituted phenyl group or pharmaceutically acceptable salts thereof.

8. The compound according to claim 7, wherein R$_{10}$ represents an isopropyl group, NR$_7$R$_8$ represents a 2-hydroxyethylamino group and Z' represents a phenyl group unsubstituted or substituted with 1 to 2 substituent groups selected from halogen or lower alkyl group, or pharmaceutically acceptable salts thereof.

9. The compound according to claim 8, wherein Z' is unsubstituted phenyl or a 4-chlorophenyl-2-methyl group or a 4-fluorophenyl group, or pharmaceutically acceptable salts thereof.

10. A pharmaceutical composition comprising the compound according to any one of claims 5 or 6 or a pharmaceutically acceptable salt thereof as an active ingredient, and a pharmaceutically acceptable carrier.

11. A pharmaceutical composition comprising the compound according to claim 7, or a pharmaceutically acceptable salt thereof as an active ingredient, and a pharmaceutically acceptable carrier.

12. A pharmaceutical composition comprising the compound according to claim 8, or a pharmaceutically acceptable salt thereof as an active ingredient, and a pharmaceutically acceptable carrier.

13. A pharmaceutical composition comprising the compound according to claim 9, or a pharmaceutically acceptable salt thereof as an active ingredient, and a pharmaceutically acceptable carrier.

14. A method for treatment of pollakiuria or urinary incontinence, which comprises administering to a patient having pollakiuria or urinary incontinence an effective amount of a compound having the formula (1):

(1)

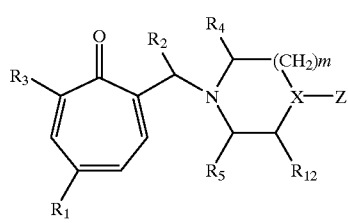

where R$_1$ represents a hydrogen atom or an unsubstituted lower alkyl group, R$_2$ represents a hydrogen atom, R$_3$ represents —OR$_6$ or —NR$_7$R$_8$, R$_6$ represents a hydrogen atom, a substituted or unsubstituted lower alkyl group, or an unsubstituted aralkyl group or an unsubstituted C$_1$ to C$_5$ acyl group, R$_7$ and R$_8$ are the same or different and represent a hydrogen atom, a lower alkyl group which may be substituted with a hetero atom, or an unsubstituted aralkyl group, or R$_7$ and R$_8$ are combined to form a 5- to 7-membered ring which may contain 1 to 3 —O— or —NR$_9$— residues, R$_9$ represents a hydrogen atom or an unsubstituted lower alkyl group; R$_4$ and R$_5$ represent a hydrogen atom, R$_{12}$ represents a hydrogen atom or a lower alkyl group, X represents a nitrogen atom, Z represents —CH(Ar$_1$)(Ar$_2$), an unsubstituted or substituted phenyl, an unsubstituted benzyl, or an unsubstituted 2-pyridyl group, Ar$_1$ and Ar$_2$ are substituted or unsubstituted aryl groups which may be the same or different, and m is 1.

15. The method for treatment of pollakiuria or urinary incontinence according to claim 14, wherein the compound is represented by the formula (2):

(2)

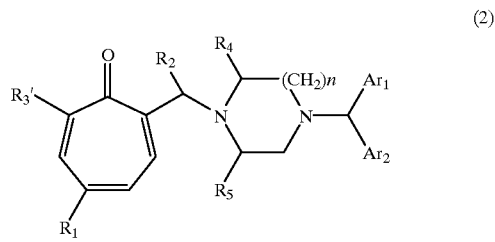

where R$_1$ represents a hydrogen atom or a lower alkyl group, R$_2$ represents a hydrogen atom, R$_3$' represents —OR$_6$, or —NR$_7$R$_8$, R$_6$' represents a hydrogen atom, a lower alkyl group which may be substituted with a hetero atom, or an unsubstituted aralkyl group, R$_7$ and R$_8$ are the same or different and represent a hydrogen atom, a lower alkyl group which may be substituted with a hetero atom, or an unsubstituted aralkyl group, or R$_7$ and R$_8$ are combined to form a 5- to 7-membered ring which may contain 1 to 3 —O— or —NR$_9$— residues, R$_9$ represents a hydrogen atom or a lower alkyl group; R$_4$ and R$_5$ represent a hydrogen atom, Ar$_1$ and Ar$_2$ are the same or different and represent a substituted or unsubstituted aryl group, and n is 1.

16. The method for treatment of pollakiuria or urinary incontinence according to claim 15, wherein R$_1$ represents an isopropyl group, R$_3$' represents a 2-hydroxyethylamino group, Ar$_1$ and Ar$_2$ independently represent a phenyl group or a 4-fluorophenyl group.

* * * * *